US012576289B2

(12) United States Patent
Murphy et al.

(10) Patent No.: US 12,576,289 B2
(45) Date of Patent: Mar. 17, 2026

(54) SYSTEMS AND METHODS FOR RELIABLE REPLACEMENT OF ULTRASOUND NEUROMODULATION WEARABLES

(71) Applicant: ATTUNE NEUROSCIENCES, INC., Menlo Park, CA (US)

(72) Inventors: Keith R. Murphy, San Francisco, CA (US); Cameron H. Good, Joppa, MD (US); Jason M. Giddings, Torrance, CA (US)

(73) Assignee: ATTUNE NEUROSCIENCES, INC., Menlo Park, CA (US)

( * ) Notice: Subject to any disclaimer, the term of this patent is extended or adjusted under 35 U.S.C. 154(b) by 0 days.

(21) Appl. No.: 18/916,169

(22) Filed: Oct. 15, 2024

(65) Prior Publication Data

US 2025/0121216 A1    Apr. 17, 2025

Related U.S. Application Data

(60) Provisional application No. 63/544,421, filed on Oct. 16, 2023.

(51) Int. Cl.
*A61N 7/00*            (2006.01)
(52) U.S. Cl.
CPC ........ *A61N 7/00* (2013.01); *A61N 2007/0026* (2013.01); *A61N 2007/0078* (2013.01)
(58) Field of Classification Search
CPC .................................................... A61N 7/00
See application file for complete search history.

(56) References Cited

U.S. PATENT DOCUMENTS

| | | | |
|---|---|---|---|
| 2012/0083717 A1* | 4/2012 | Alleman | A61B 8/546 601/2 |
| 2020/0054414 A1 | 2/2020 | Wagner | |
| 2021/0060330 A1 | 3/2021 | Chu | |
| 2021/0330294 A1 | 10/2021 | Hynynen | |
| 2023/0149684 A1 | 5/2023 | Sadik | |
| 2023/0149746 A1 | 5/2023 | Peters | |
| 2023/0166129 A1 | 6/2023 | Murphy | |

OTHER PUBLICATIONS

International Search Report of PCT/US2024/051413, Mailed Jan. 30, 2025, (26 pages).

* cited by examiner

*Primary Examiner* — Joseph M Santos Rodriguez
(74) *Attorney, Agent, or Firm* — NIXON PEABODY LLP

(57) ABSTRACT
Systems and methods for reliably returning a neuromodulation system to a predetermined position relative to a user's head is disclosed. The system includes a neuromodulation device and a stimulation control computing environment. The stimulation control computing environment can be configured with data processing functions to focus ultrasound emission to a target brain region. The system identifies an initial position of one or more ultrasound-emitting elements with respect to the head of a user, uses brain images to identify the target brain region, and performs acoustic simulations to focus ultrasound emissions from the initial position to the target brain region. The distance between an inner surface of the device and a user's head can be measured, and one or more spacing elements can be placed on the inner surfaces based on the measured distances, which enables the reliable return of the neuromodulation device to the initial position with minimal displacement.

24 Claims, 13 Drawing Sheets

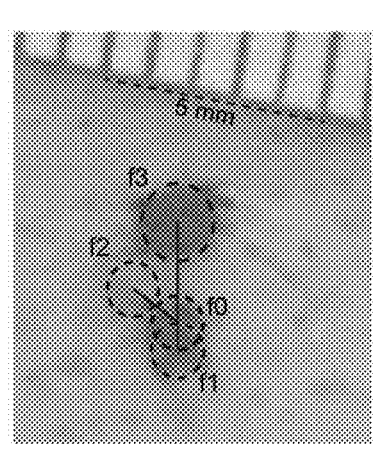
FIG. 5A
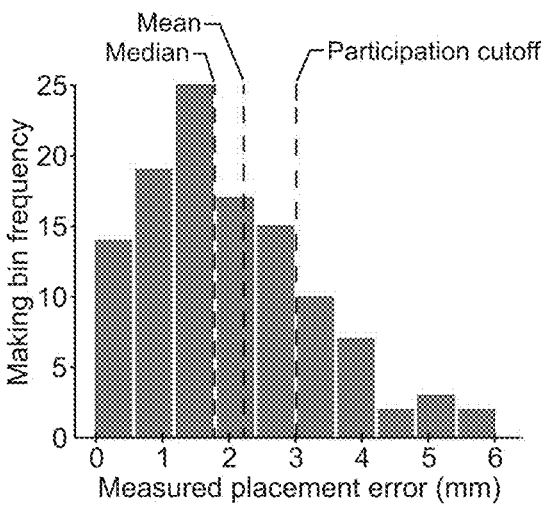
FIG. 5B
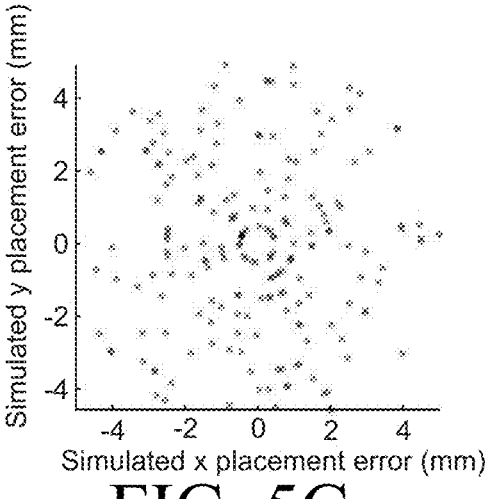
FIG. 5C
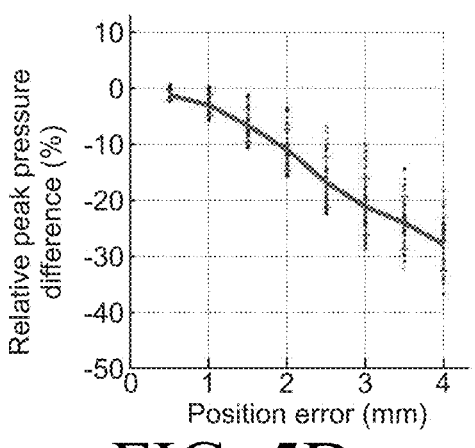
FIG. 5D
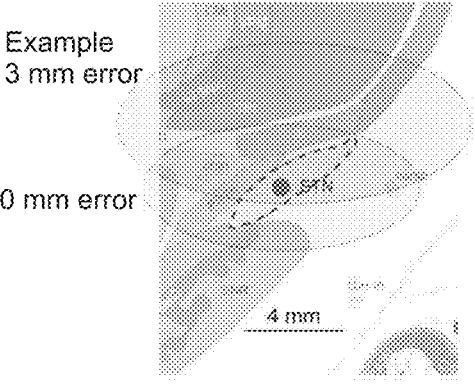
FIG. 5E
FIG. 5F

SYSTEMS AND METHODS FOR RELIABLE REPLACEMENT OF ULTRASOUND NEUROMODULATION WEARABLES

RELATED APPLICATIONS

This application claims the benefit of U.S. Provisional Patent Application No. 63/544,421 filed on Oct. 16, 2023, which is incorporated by reference herein in its entirety. This application is related to U.S. Non-Provisional application Ser. No. 17/332,934, entitled "Ultrasound Systems and Associated Devices and Methods for Modulating Brain Activity" and filed on May 27, 2021, which is incorporated herein by reference. This application is also related to U.S. Non-Provisional application Ser. No. 18/071,472, entitled "Head-Wearable Devices for Positioning Ultrasound Transducers for Brain Stimulation" and filed on Nov. 29, 2022, which is incorporated herein by reference.

FIELD

The present disclosure generally relates to systems and methods for reliably returning a head-mounted neuromodulation device to a predetermined position to facilitate accurately recreating an ultrasound focus at a target brain region.

BACKGROUND

Multiple ultrasound waves can constructively interfere, or focus, at a distance from their sources using the same principles that allow light to be focused through a lens. To accomplish this, an array of individual ultrasound elements, or sources, can focus ultrasound waves into a restricted region by assigning different time or phase delays to the waves passed onto each element. These delays can partially mimic the effect of physical curvature normally used to achieve focusing. The pressure created at the resulting focus can be sufficient to engage mechanosensitive channels which regulate neuronal membrane potential to either inhibit or excite neurons directly or indirectly through neighboring cell types. By targeting the focus onto specific brain regions associated with psychiatric disorders, therapeutic effects can be achieved.

In practice, conventional therapeutic ultrasound devices with anatomically precise targeting often require real-time MRI data acquisition and acoustic simulation to identify the neural target region and properly assign time delays to each ultrasound element to enable focusing on that region. Calculating these delays can be achieved by collecting the coordinates of each ultrasound element and the target region within the MRI space, estimating acoustic properties of that space, and then assessing wave travel time from each element to the target region through time reversal, ray tracing, or similar methods. While these methods have been effective in tissue ablation or in-clinic neuromodulation, they have not typically allowed for out-of-clinic ultrasound use since the device cannot be reliably registered to the user's skull without active MRI. In theory, the ultrasound targeting achieved under MRI guidance should be applicable across uses given the stability of the human brain and skull. However, these clinical devices offer no means of returning ultrasound arrays to the same position and orientation at the time of the subsequent scans. Thus, creation of a device which allows its users to reliably return the position of the transducers would allow focused ultrasound therapy in the absence of an operator or clinician, allowing for use for nightly at home therapeutic use during normal waking activity or sleep.

The embodiments disclosed herein are directed to addressing these and other considerations.

BRIEF DESCRIPTION OF THE DRAWINGS

The present disclosure can be better understood, by way of example only, with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 5A shows the reliable return of an exemplary neuromodulation device to approximately an initial position on the head of a user, according to aspects of the present disclosure.

FIG. 5B depicts the measured placement error of subsequent replacements of the neuromodulation device, according to aspects of the present disclosure.

FIG. 5C depicts the relationship between placement errors along the x-axis and placement errors along the y-axis, according to aspects of the present disclosure.

FIG. 5D depicts the relationship between relative peak pressure produced by the neuromodulation device at a target brain area and the position error, according to aspects of the present disclosure.

FIG. 5E depicts the relationship between beam volume produced by the neuromodulation device at a target brain area and the position error, according to aspects of the present disclosure.

FIG. 5F depicts comparisons of exemplary beam cross section produced by the neuromodulation device at a target brain area with no error and approximately 3 mm position error, according to aspects of the present disclosure.

DETAILED DESCRIPTION

Figure 1A:
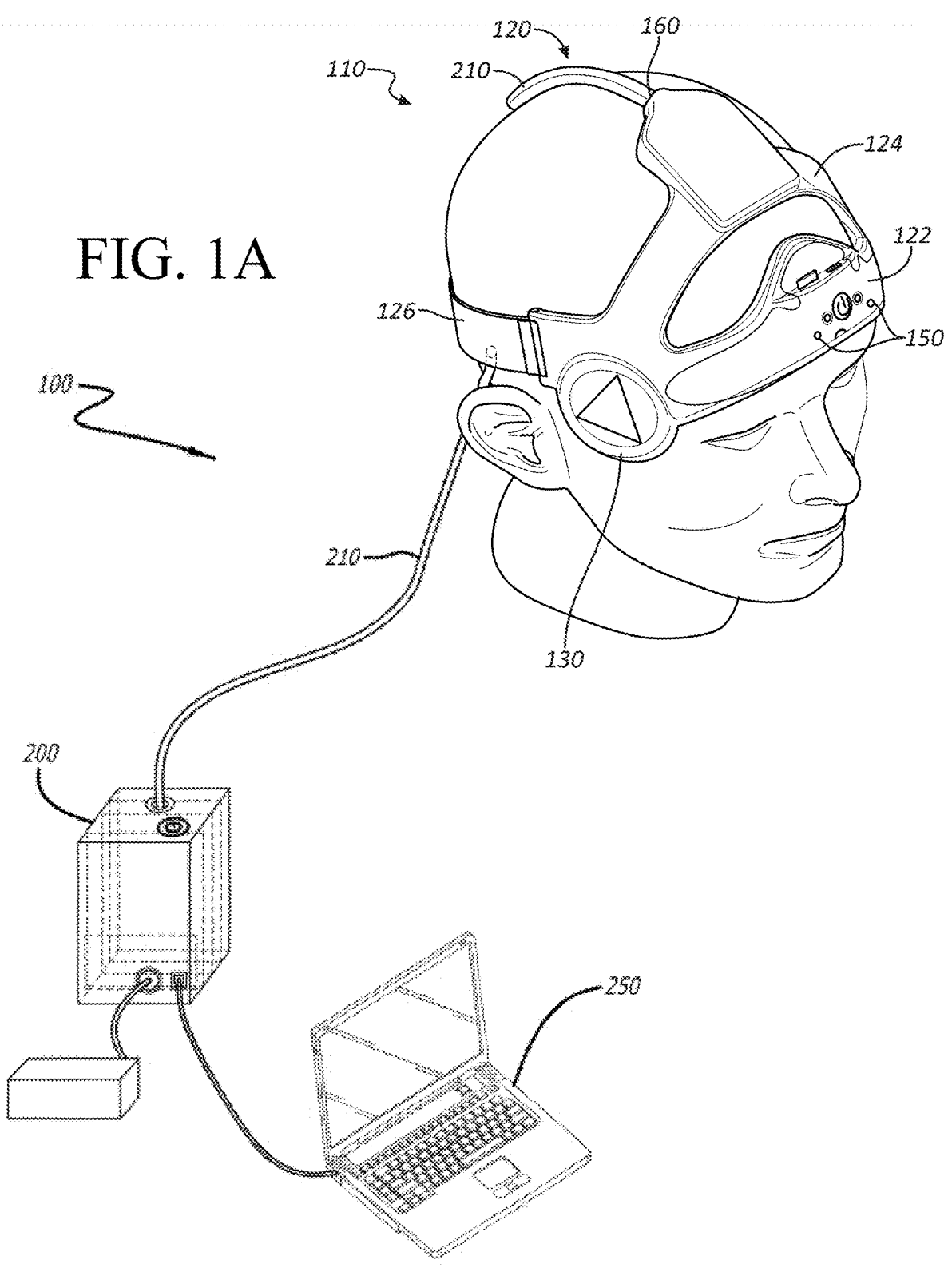
FIG. 1A shows a neuromodulation device and a stimulation control computing environment according to aspects of the present disclosure.

The present specification discloses systems and methods for reliably returning the position of transducers of a neuromodulation system to approximately a predetermined position. Embodiments consistent with the present disclosure address the need for systems and methods for reliably returning a head-worn neuromodulation device to a known position relative to the user's head and for enabling ultrasound focus to be reliably recreated approximate a target region of the user's brain for focused ultrasound modulation after removal and refitment of the device. The neuromodulation system can comprise a wearable neuromodulation device integrated with EEG electrodes and one or more integrated ultrasound transducer arrays. The disclosed neuromodulation system can further include a stimulation control unit comprising one or more processors, and software that operates and controls the features and functionality of the ultrasound stimulation when executed by such processors. Such software includes, without limitation, EEG real-time analysis software that can continuously monitor brain functionality to identify one or more certain characteristics, phases or states of brain activity, and brain mapping software that can plot one or more specific region of the brain and accurately focus or steer ultrasound stimulation to that one or more specific brain regions. The disclosed neuromodulation system also includes a computational device that aids in neuromodulation device operation and data storage of collected information. Thus, a neuromodulation system disclosed herein noninvasively administers ultrasound stimulation in a spatially and temporally controlled manner.

As such, a device disclosed herein enables a focus application of ultrasound stimulation to a specified region of the brain that largely excludes surrounding brain tissue.

The disclosed neuromodulation device can be coupled to brain substructure mapping software that identifies one or more specific regions to be targeted for ultrasound stimulation. In some embodiments, one or more specific regions of the brain are identified by comparing a brain image scan to a brain atlas which may be publicly available or internally annotated to identify a common coordinate space. The system can use brain image scans, including scans generated by computed tomography (CT) and magnetic resonance imaging (MRI) to determine a position of the one or more transducer elements relative to the temple of a user. Non-limiting sources of such brain image scans include scans obtained from a user of a neuromodulation device disclosed herein (personalized model customized for a particular user), scans obtained from deidentified individuals through healthcare facilities, or scans obtained from deidentified individuals through registries like the Human Connectome. Brain image scans are registered with a common brain region atlas and image segmentation performed to identify centroids in voxel space of the one or more specific regions to be targeted for ultrasound stimulation. In some embodiments, the target brain region is the thalamus. In some embodiments, the one or more specific regions to be targeted for ultrasound stimulation is a sub-region of the thalamus such as, but not limited to the central nucleus of the thalamus, the reticular thalamus, the subthalamic nucleus, the lateral thalamus, or some combination thereof.

In some embodiments, the position of one or more ultrasound transducer elements relative to the temporal window (e.g., temple of a user) can be identified using biometric parameters (e.g., fiducial landmark elements). The position of the one or more transducers relative to the temporal window (e.g., the temple of a user) may be estimated as a point in 3D space relative to a fiducial landmark element which have some predictive value for the positioning of the ultrasound transducer elements relative to the temporal window. This biometric may include, but is not limited to, the position of a person's eyes, ears, eyebrow ridge, nose, mouth, jawline, or other appendage relative to a cranial landmark. This biometric may also include a relative point along a cranial feature axis, such as a fractionally defined mid-point along the forehead, between the ears and eyes, between the corner of the mouth to the base of the ear, or some other combination of cranial features or appendages.

Once the one or more specific target brain regions are identified, a brain substructure mapping software disclosed herein can identify the coordinate space of each transducer elements within the image data. According to some embodiments, the system can register the initial position of the one or more ultrasound transducer elements relative to the temporal window using one or more fiducial landmark elements as described above. The system may then accurately calculate the temporal phase offset of ultrasound transducer elements by estimating acoustic temporal path length between the element and the target brain regions of one or more identified locations or by performing a full wave simulation. Initially the software may determine acoustic impedance by employing an algorithm that converts pixels of a brain image scan from the brain modeling database into measurements of acoustic impedance (Hounsfield units). A brain substructure mapping software may determine the appropriate phase of ultrasound emissions form the one or more ultrasound transducer elements required to effectively apply ultrasound stimulation onto a target brain region. In some embodiments, the required beam steering is determined by modeling simulations of wave equations by estimating the temporal wave path length to the target brain area, accounting for difference in sound speed across skull and tissue as well as wave refraction. The simulation then adjusts the excitation phase delay of each ultrasound transducer element until the wave fronts constructively interfere at the focus. This process may be referred to herein in shorthand as computing and applying a phase change to ultrasound emissions to create an ultrasound focus at a target brain region.

Once the initial position of the one or more ultrasound transducer elements relative to the temporal window is determined, the neuromodulation device can accurately focus ultrasound emissions from the one or more ultrasound transducer elements to the target brain region as long as the one or more ultrasound transducer elements remain approximately at the initial position. A significant shift away from the initial position can cause the determined temporal phase offsets of the ultrasound transducer elements to be incorrect, causing the ultrasound focus formed at the target brain region to be attenuated.

Accordingly, embodiments of the present disclosure solve this problem by introducing spacing elements that are positioned on the inner surface of the neuromodulation device that are custom fitted for the user of the device. Before the initial position of the ultrasound transducer elements is determined, the device can be fitted onto the user, and a depth measuring gauge can be used to measure gap distances between the inner surface sections of the band of the neuromodulation device and the head of the user. In some embodiments, the gap distance can be assessed in ways beyond a direct measurement. For example, assessing the gap distance can be based on a user's subjective opinion of the fit, a user's subjective measure of the comfort of the device, and/or based on a visual inspection of the device fitment. One or more spacing elements are fitted to the inner surface of the band of the neuromodulation device. These spacing elements cause the neuromodulation device to have a snug fit which allows for the replacement of the neuromodulation device on the head of the user such that the ultrasound transducer elements reliably return to approximately the initial position with respect to the temporal window of the user. Accordingly, using the systems and methods disclosed herein, the neuromodulation system can be utilized by users without active imaging techniques.

According to some embodiments of the present disclosure, the problem of shifting transducer elements during wear of the neuromodulation device is addressed by designing the neuromodulation device to have a specific angular relationship between a frontal contact point at which the neuromodulation device contacts the head of a user and the top contact point at which the neuromodulation device contacts the head of the user, as well as a specific angular relationship between the top contact point at which the neuromodulation device contacts the head of the user and a rear contact point at which the neuromodulation device contacts the head of the user. That is, to minimize shifting of the neuromodulation device during use and wear, some embodiments of the present disclosure provide for an angle between approximately 45 degrees and 55 degrees that is formed between the frontal contact point and the top contact point. In some embodiments, to minimize shifting of the neuromodulation device during use and wear, the neuromodulation device can be provided having an obtuse angle formed between the top contact point and the rear contact point. Optimal angular relationships for the head-worn neuromodulation device are based on minimizing the moment of inertia experienced by the neuromodulation device during wear, as will be described in more detail below. Some implementations of the disclosed technology will be described more fully with reference to the accompanying drawings. This disclosed technology may, however, be embodied in many different forms and should not be construed as limited to the implementations set forth herein. The components described hereinafter as making up various elements of the disclosed technology are intended to be illustrative and not restrictive. Many suitable components that would perform the same or similar functions as components described herein are intended to be embraced within the scope of the disclosed electronic devices and methods.

Figure 1B:
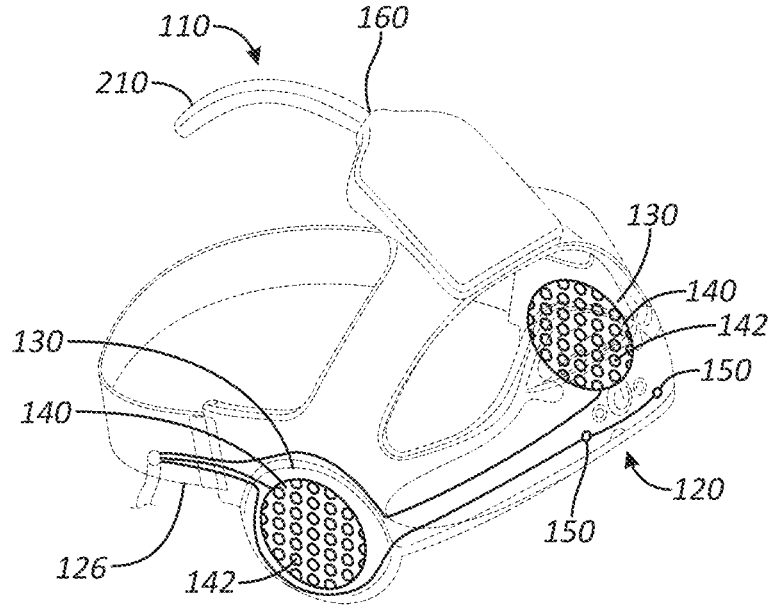
FIG. 1B shows exemplary hardware components of a neuromodulation device according to aspects of the present disclosure.

In some embodiments, and as shown in FIGS. 1A-B, an exemplary neuromodulation device 110 can include a wearable device housing 120, which can support two array housings 130 each containing an ultrasound transducer array 140, and may include two EEG electrodes 150, such as, e.g., active dry EEG electrodes. When worn, wearable device housing 120 is configured to encircle the head in a transverse plane that positions the main band along the forehead, temples and back of the head. Wearable device housing 120 provides rigid stereotactic placement of ultrasound transducer arrays 140 over the temporal window 232 of the user's head as well as positions EEG electrodes 150 flat against the user's forehead. According to some embodiments, the EEG electrodes 150 can be used to measure cortical brain activity during sleep.

Wearable device housing 120 can include a main band 122, a secondary band 124, and an optional securing strap 126. Main band 122, secondary band 124 and securing strap 126 can be adjustable to facilitate accurate positioning and securing of neuromodulation device 110 to a user's head. Secondary band 124 can be attached to main band 122 via first and secondary band attachment points and configured to extend over the top of the head. First and second band attachment points can be static or configured to allow movement between secondary band 124 and main band 122. Optional securing strap 126 is attached to main band 122 via first and second securing strap attachment points and configured to extend under the chin. First and second securing strap attachment points can be static or configured to allow movement between securing strap 126 and main band 122. In aspects of these embodiments, main band 122 has front and back portions composed of a semi-rigid material and side or temple portions composed of a flexible material, secondary band 124 and a first and second attachment hubs each being composed of a semi-rigid material, and a securing strap being composed of an elastic material. Although the embodiment shown in FIGS. 1A-B includes optional securing strap 126, it should be understood that in some embodiments, the optional securing strap 126 is omitted, and in yet other embodiments, optional securing strap 126 is replaced with a band similar to the construction of main band 122 and/or secondary band 124. Similarly, in some embodiments, main band 122 and secondary band 124 may be of unitary construction. In other words, a single band may extend from approximate the forehead of a user to the top of the head, as shown and described in more detail with respect to FIG. 7B. In yet other embodiments, wearable device housing 120 can include a single band that stretches from approximate the forehead Neuromodulation device 110 can include one or more ultrasound transducer arrays 140 contained in a housing attached to main band 122 of wearable device housing 120. The one or more ultrasound transducer arrays 140 can be located on the inner surface of main band 122 and configured to interface with a user's head. In some embodiments, a neuromodulation device disclosed herein contains a single ultrasound transducer array 140 located on the main band. In some embodiments, neuromodulation device 110 contains a single ultrasound transducer array 140 located on one side of main band 122 positioned at either the left or right temple region of a user above the ears. In some embodiments, neuromodulation device 110 contains a single ultrasound transducer array located on each side of main band 122 positioned at the left and right temple region of a user above the ears. In some embodiments, neuromodulation device 110 contains multiple ultrasound transducer arrays 140 located on each side of main band 122 positioned at the left and right temple region of a user above the ears. In aspects of these embodiments, and as shown in FIG. 1A-B, neuromodulation device 110 comprises two ultrasound transducer arrays 140 one located on the left side of main band 122 and one located on the right side of main band 122. In aspects of these embodiments, neuromodulation device 110 comprises two ultrasound transducer arrays 140 located on the left side of main band 122 and two ultrasound transducer arrays 140 located on the right side of main band 122. It should be understood, that while each ultrasound transducer array 140 is shown having a plurality of ultrasound-emitting elements 142, in some embodiments, each ultrasound transducer array 140 can comprise a single ultrasound-emitting element 142. In some embodiments, the neuromodulation device 110 can optionally include photoplethysmography (PPG) sensors (not shown). In some embodiments, the neuromodulation device 110 can include one or more accelerometers (not shown) that may be used to capture head movement of a user wearing the neuromodulation device 110.

In some embodiments, custom padding and a detachable fit tool (shown in FIGS. 2A-2E) allow the neuromodulation device 110 to maintain consistent, repeated positioning of the transducers across sessions. The ultrasound-emitting elements 142 can be designed to interface with the "temporal window" 232, a thin portion of skull bone posterior to the eyes that allows access to centralized deep brain structures. In some embodiments, the neuromodulation system 100 determines ultrasound beam steering parameters that are unique to each person's brain and skull morphology that are used to accurately target certain brain regions with FUS. In some embodiments, the neuromodulation system 100 utilizes a combination of custom automated MRI scan segmentation, transducer spatial mapping, and acoustic simulation tools to optimize off-line targeting of brain regions.

As shown in FIGS. 1A-B, neuromodulation device 110 can contain EEG electrodes 150 located on the inner surface of main band 122 and configured to interface with a user's head. In some embodiments, neuromodulation device 110 contains a single EEG electrode 150 located on the front portion of main band 122 positioned at the forehead of a user above the eyebrows. In some embodiments, neuromodulation device 110 contains multiple EEG electrodes 150, each located on the front portion of main band 122 positioned at the forehead of a user above the eyebrows. In aspects of these embodiments, and as shown in FIGS. 1A-B, neuromodulation device disclosed herein comprises two EEG electrodes 150 each located on the front portion of main band 122 with one positioned above the left eyebrow of a user and the other positioned above the right eyebrow of the user. However, it should be understood that in other embodiments, the number and specific positioning of EEG electrodes 150 can be varied.

A single EEG electrode, or a plurality of EEG electrodes comprising a neuromodulation device disclosed herein provides sufficient sensitivity to provide optimal measurement of brainwave activity, including, without limitation, wave frequency, wave amplitude, and waveform type to effectively identify one or more characteristics, phases or states of brain activity. In aspects of this embodiment, a neuromodulation device disclosed herein comprises a plurality of EEG electrodes having sufficient sensitivity to detect and measure alpha waves, beta waves, theta waves, delta waves, gamma waves, sleep spindles, K complexes, or any combination thereof.

Neuromodulation device 110 can comprise a planar, open-curved arc, or closed-curved arc configuration of EEG electrodes. The planar, open-curved arc, or closed-curved arc configuration of EEG electrode is a configuration designed to provide optimal measurement of brainwave activity, including, without limitation, wave frequency, wave amplitude, and waveform type to effectively identify one or more characteristics, phases or states of brain activity. In some embodiments, a neuromodulation device disclosed herein is a one-dimensional planar, curved or closed curved arc configuration of EEG electrodes. In some embodiments, each EEG electrode can be controlled in isolation, or in clusters to reduce cabling.

A neuromodulation device disclosed herein further contains conductive wiring. Such conductive wiring can be located exteriorly on the device housing or embedded within wearable device housing 120, such as, e.g., within a channel, and will exit the housing through a port located at the back. In some embodiments, the conductive wiring will exit cable port 160 parallel to the head in the anterior-posterior direction allowing the user to lay on his back against the flush wires. Conductive wiring disclosed herein powers an EEG amplification stage for each EEG electrode 150, each ultrasound transducer array 140, stimulation control unit 200 and its associated processing elements and functions, and other components of neuromodulation device 110 and can be bundled together. In some embodiments, conductive wiring runs through a channel within main band 122 connecting each EEG electrode 150 to one or more amplifiers, a digital analog converter, and a stimulation control unit 200 before exiting via cable port 160 located at a back portion of main band 122. In some embodiment, and with respect to each ultrasound transducer array 140, conductive wiring runs through a channel within main band 122 connecting each ultrasound transducer array 140 to stimulation control unit 200 before exiting via cable port 160 located at a back portion of main band 122.

Aspects of the present specification disclose a neuromodulation system comprising a stimulation control computing environment including a stimulation control unit and a computing device. Referring to FIG. 1A, neuromodulation system 100 further contains a stimulation control unit 200 located on main band 122 or tethered to main band 122 with conductive wiring 210 via a cable port 160. Stimulation control unit 200 comprising a central control application-specific integrated circuits (ASIC) processor, a printed circuit board (PCB) component which contains an ultrasound phase control component, one or more signal amplifiers, an ultrasound matching network as well as a power source and other processors. The ASIC chip processes EEG data, ultrasound state data, ultrasound-emitting element target phase data, power usage, and data storage. This ASIC processor sends information regarding element phase which triggers the ultrasound phase control component and one or more signal amplifiers of the PCB component. This PCB component then sends signals to the ultrasound matching network to reduce reflections from acoustic impedance mismatch and then to each ultrasound-emitting element 142 of ultrasound transducer array 140, which allow for beam steering on neuromodulation device 110. Stimulation control unit 200 uses an input file regarding phase delays for each target structure, which can be subdivisions of a single target as well as a stimulation protocol for each target. This file is loaded through a bus interface, such as, e.g., a LIGHTNING connector, a micro-USB connector, a USB-C connector, and the like, and is derived through acoustic simulations performed on a brain image set of the user wearing neuromodulation device 110. The simulation maps patient's target brain regions relative to ultrasound-emitting elements 142 of each ultrasound transducer array 140 and appropriately phase corrects each element timing such that a beam focuses on the target.

Referring to FIG. 1A, a stimulation control computing environment disclosed herein also comprises a computing device 250 and an algorithmic framework including one or more processors and a plurality of software and hardware components (including a digital analog converter, function generator, and hard drive) configured to execute program instructions or routines to perform the data processing and performance functions that controls the operability of a neuromodulation device disclosed herein. In certain embodiments, computing device 250 can comprise an offline computing device. In certain embodiments, computing device 250 can comprise a cloud computing environment that is connected to other components of the neuromodulation system 100 over a network, such as the Internet.

An algorithmic framework of stimulation control unit 200 and software elements disclosed herein is part of the one or more systems and methods that apply mathematical functions, models or other analytical and data processing techniques in real-time to ensure a neuromodulation device disclosed herein applies ultrasound stimulation in an appropriate spatial and temporal manner to one or more specific regions of the brain separately and differentially in response to the brain activity data obtained by an EEG electrode.

It should be noted that processing of data and algorithms described herein may be performed by system components implemented in hardware or a combination of hardware and software (see exemplary description of components in FIGS. 1A-1B). As an example, such system and component may include at least one processor, such as a digital signal processor (DSP) or central processing unit (CPU), configured to execute instructions stored in memory for performing the functions described herein. In some embodiments, ASIC or gate arrays, such as field-programmable gate arrays (FPGAs), may be used to implement any of the functions described herein. Various configurations of circuitry for the processing of data and algorithms described here are possible.

Figure 1C:
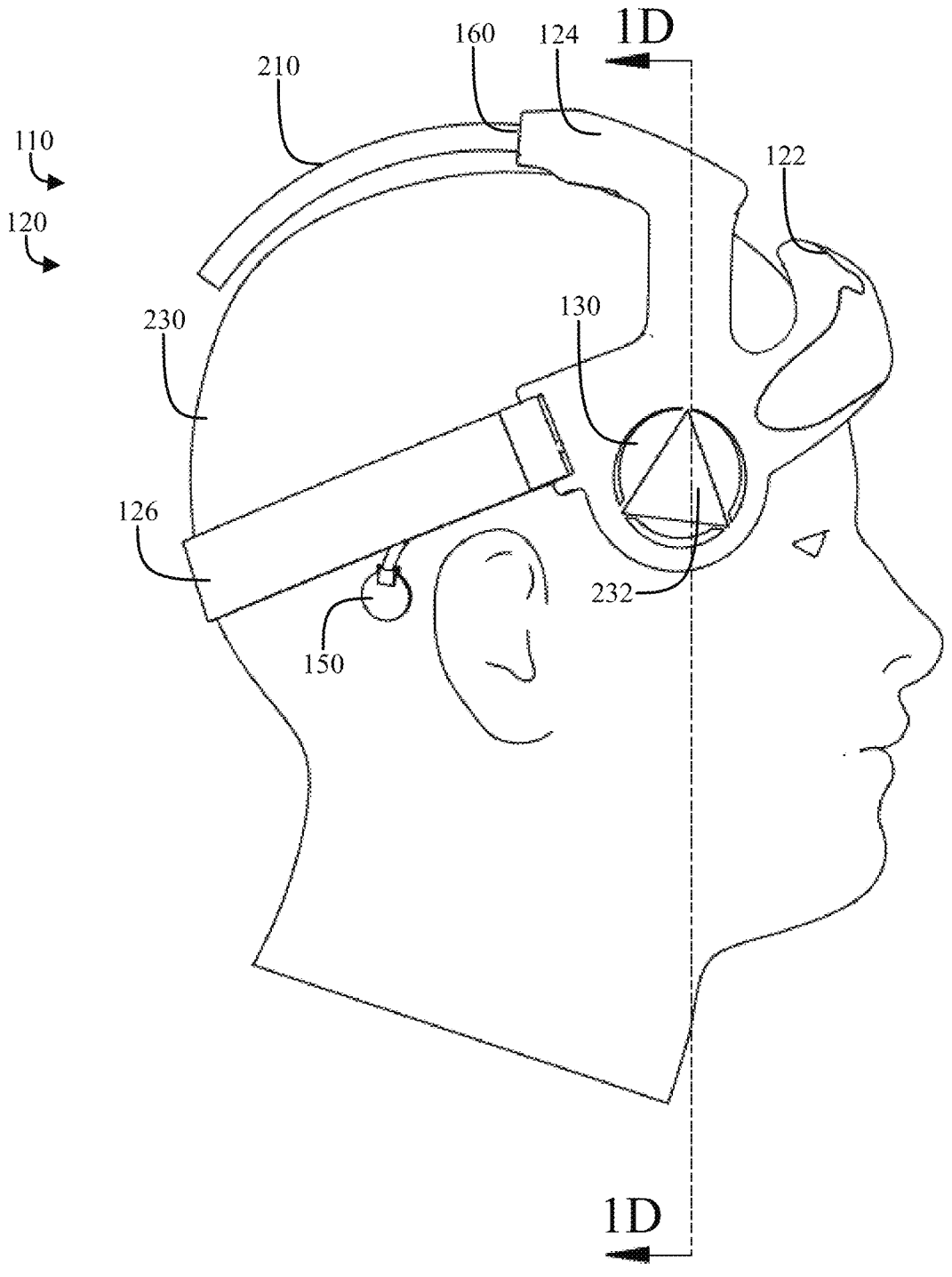
FIG. 1C shows an exemplary neuromodulation device fitted to a user, according to aspects of the present disclosure.
Figure 1D:
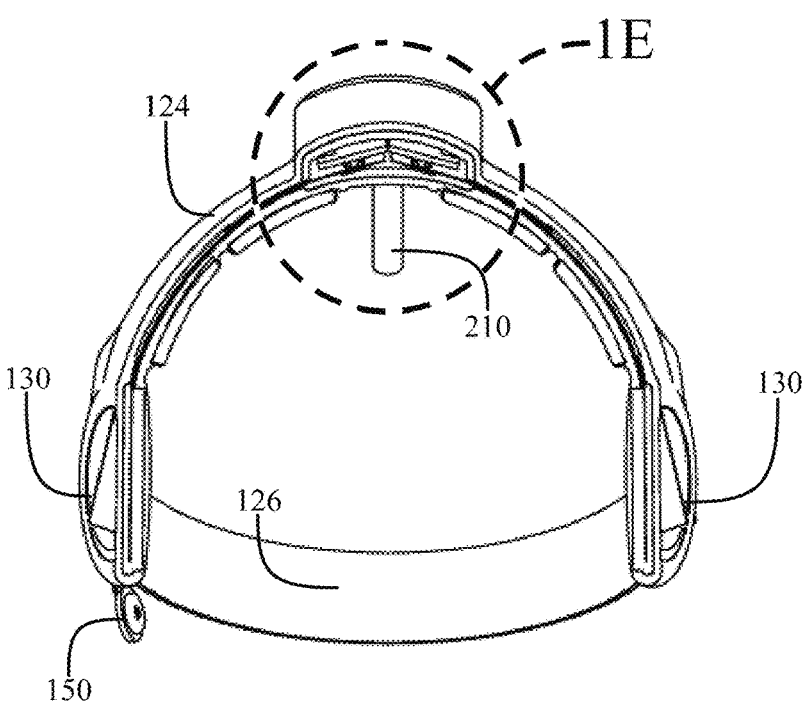
FIG. 1D shows various details of the neuromodulation device of FIG. 1C, according to aspects of the present disclosure.
Figure 1E:
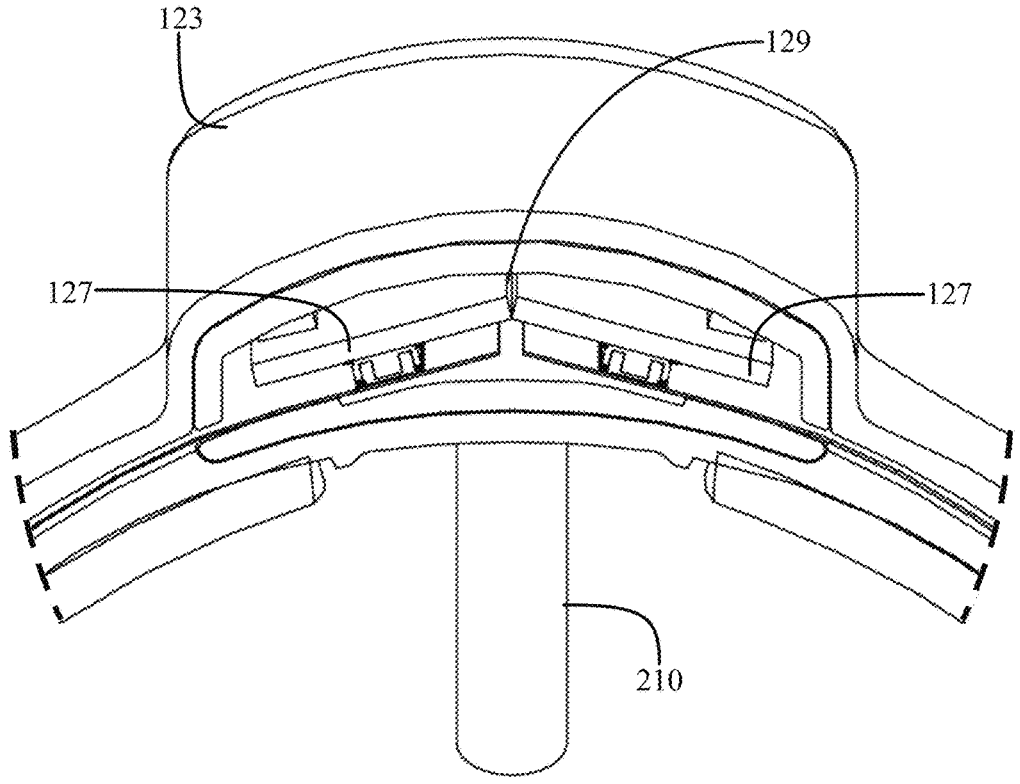
FIG. 1E shows various details of the neuromodulation device of FIG. 1C, according to aspects of the present disclosure
Figure 3:
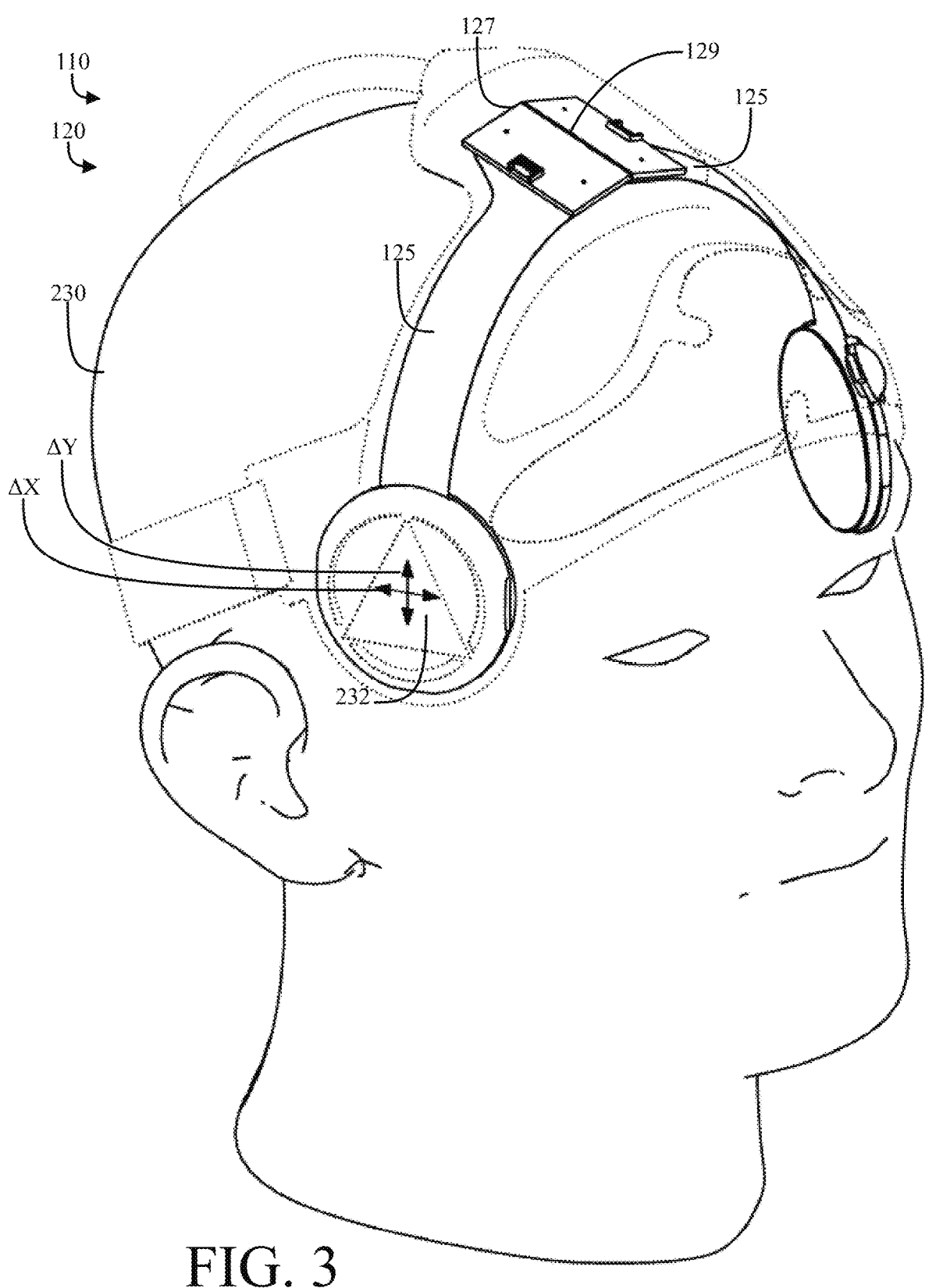
FIG. 3 depicts the shift of an exemplary neuromodulation device between an initial placement on a user and a subsequent replacement of the neuromodulation device on the user, according to aspects of the present disclosure.

FIG. 1C shows another embodiment of the exemplary neuromodulation device 110 and FIGS. 1D and 1E show various details of the neuromodulation device as shown in FIG. 1C. As shown in FIG. 1C, the neuromodulation device 110 can include wearable device housing 120. Wearable device housing can include a main band 122, a secondary band 124, and an optional securing strap 126. In contrast to the embodiment shown in FIGS. 1B, the optional securing strap 126 of FIG. 1C can be positioned around the back of the user's head 230 rather than under the chin as shown in FIGS. 1A-1B. The secondary band 124 can be attached to the main band via first and second secondary band attachment points and configured to extend over the top of the head. As shown in FIG. 1C, neuromodulation device disclosed herein can include EEG electrodes 150 each located below optional securing strap 126 and behind the ear of a user's head 230. However, it should be understood that in other embodiments (e.g., as shown in FIGS. 1A-1B), the number and specific positioning of EEG electrodes 150 can be varied. As discussed with respect to FIGS. 1A-1B, the wearable device housing 120 can support two array housings 130 which each can contain an ultrasound transducer array 140. As discussed above, wearable device housing 120 includes cable port 160 through which conductive wiring 210 exits the wearable device housing 120. In contrast to the embodiment shown in FIGS. 1A-1B, the conductive wiring 210 and the cable port 160 can be positioned such that the conductive wiring 210 exits the cable port 160 and can extend towards the posterior side of the user's head 230 from the top or sides of the neuromodulation device 110 as illustrated on the secondary band 124. As will be discussed with respect to FIG. 4, the angle between the conductive wiring 210 and the user's head can form an angle of no more than approximately 15 degrees relative to the parallel surface of the top of the user's head 230. FIG. 1D shows the cross section of neuromodulation device 110, and FIG. 1E is an enlarged detail view of FIG. 1D showing the band housing 123 in more detail. As can be seen in FIGS. 1D-1E, secondary band 124 can contain a conductive internal portion 125 (FIG. 3). Further connecting respective left and right portions of the conductive internal portion 125 is a flexible circuit 127 within the band housing 123. Notably, respective left and right portions of flexible circuit 127 are joined by joint 129. The functionality of the conductive internal portion 125, flexible circuit 127, and joint 129 will be described in more detail with respect to FIG. 3.

Figures 2A, 2B, 2C:
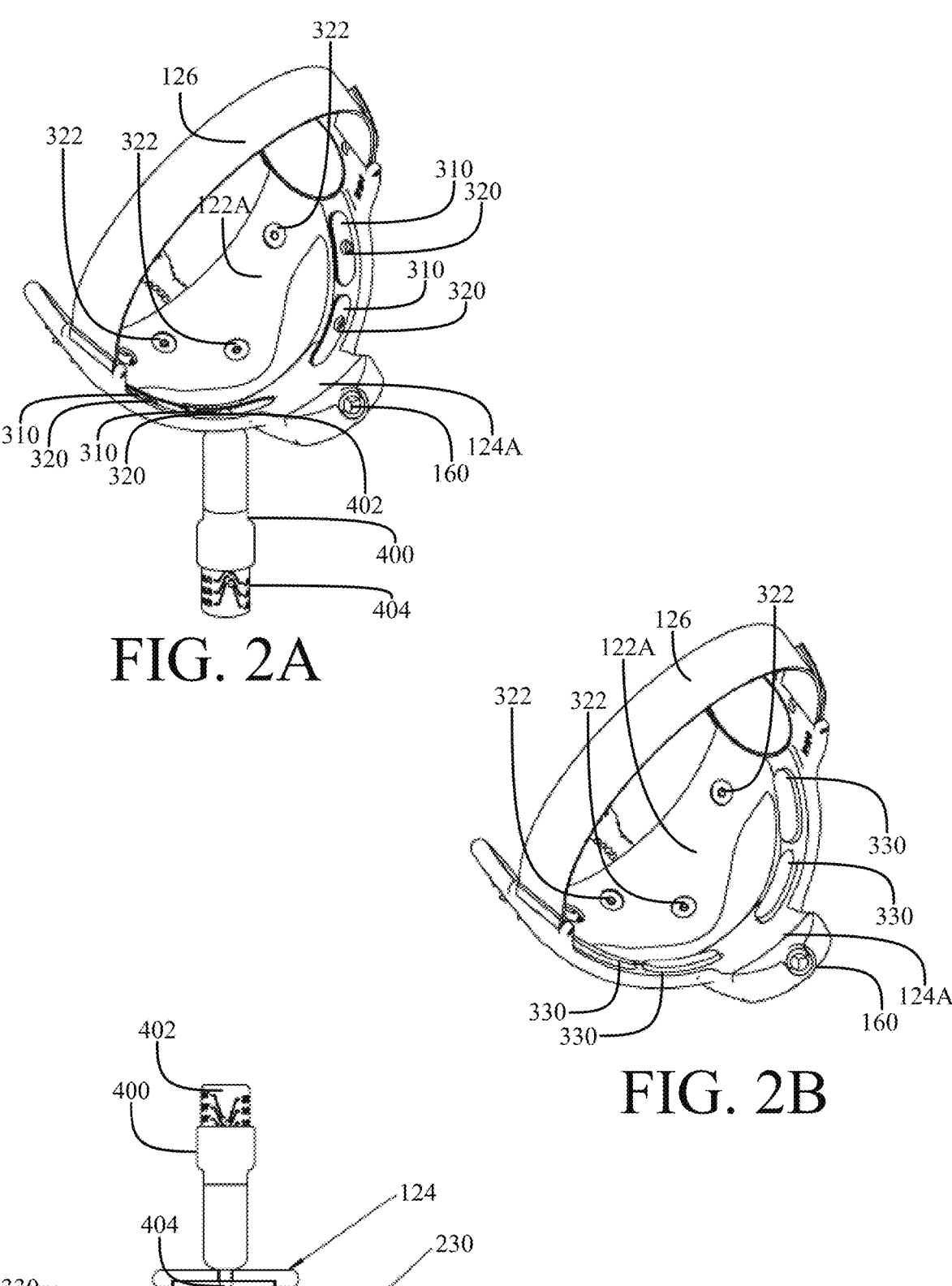
FIG. 2A depicts an exemplary procedure for determining gap distances between the exemplary neuromodulation device and the head of the user, according to aspects of the present disclosure.
FIG. 2B depicts placement of one or more spacing elements between the exemplary neuromodulation device and the head of the user, according to aspects of the present disclosure.
FIG. 2C depicts the positioning of an exemplary spacing element between the neuromodulation device and the head of the user, according to aspects of the present disclosure.

FIGS. 2A-2E depict exemplary procedures for determining gap distances between the exemplary neuromodulation device and the head 230 of the user. As shown in FIG. 2A, according to at least some embodiments, the wearable device housing 120 of the neuromodulation device 110 can include one or more inner surface sections 310 that are disposed on an inner surface 124A of the secondary band 124. Each of the one or more inner surface sections can be concave or convex with respect to the inner surface 124A of the secondary band 124. The inner surface sections 310 are configured to receive respective spacing elements that are designed to provide a snug fit of the wearable device housing 120 against the head 230 of a user such that subsequent fitments of the wearable device housing 120 to the head 230 of the user allow the ultrasound transducer elements 142 to be returned to approximately the same position as the initial position that was determined during device registration. In this regard, each of the inner surface sections 310 can include an aperture 320 through which a measurement tool (e.g., depth sensing device 400) can be used to measure a gap distance between the user's head 230 and the respective inner surface section 310. In this way, the gap distance can be determined, and a custom-sized spacing element (e.g., spacing element 330) can be selected and attached to the respective inner surface section 310. As can be seen in FIG. 2A main band 122 can also include one or more apertures 322 that the depth sensing device can be used to determine gap distance between the inner surface 122A of the main band 122 and the head 230 of the user. Optionally, inner surface 122A can include inner surface section similar to inner surface section 310. The measurement tool can be of any suitable type. The embodiment depicted in FIGS. 2A-2E show the use of measurement tool as a depth gauge 400, but it should be understood that any suitable type of measurement tool can be used in place of a depth gauge 400. According to one embodiment, the measurement tool can comprise an optical distance sensor (e.g., a laser distance finder) that can determine the gap distance as discussed above. Depth sensing device 400 can include a measurement gauge 402 and the bore tip 404 as shown in FIG. 2A. The bore tip 404 can be extended through apertures 320 and extended by rotation of the measurement gauge 402 until the bore tip 404 makes contact with the head 230 of the user while the wearable device housing 120 is worn by the user. The measurement gauge 402 can be read to determine the gap distance for each inner surface section 310. Although the secondary band 124 is shown having four inner surface sections 310, it should be understood that the size and number of inner surface section 310 can be varied as desired. In one embodiment, there can be a single inner surface section that extends along all of or a part of the inner surface 124A of the secondary band 124. As shown in FIG. 2B, based on the determined gap distances, one or more spacing elements 330 can be affixed to each respective inner surface section 310. The one or more spacing elements 330 can have a thickness that is determined based on the measured gap distance for each respective inner surface section 310. In one embodiment, the thickness of the spacing element 330 for a respective inner surface section 310 is selected to be the same or approximately the same as the determined gap distance. FIG. 2C shows a spacing element 330 that is selected based on the gap distance determined using depth gauge 400, as described above. Spacing elements can comprise various suitable materials that provide adequate comfort and do not significantly compress to provide a reliable fitment of the wearable device housing 120 on the head 230 of a user. In one embodiment, the spacing element 330 can be a high-density foam. In another embodiment, the spacing element 330 can comprise a plastic material. The spacing element 330 can be attached to the inner surface sections 310 using various means. In some embodiments, the spacing elements 330 are securely attached to the inner surface section 310 using a hook and loop system (with complementary hook and/or loop on each of the inner surface section 310 and the spacing element 330). In another embodiment, the spacing elements 330 are securely attached to the inner surface section 310 by an adhesive. In another embodiment, the spacing elements 330 can be securely attached to the inner surface sections 310 using a slotting mechanism. For example, the spacing element 330 can have a tab that is configured to securely fit into a complementary slot within the inner surface section. In another example, the spacing element 330 can have a slot, while the inner surface section 310 can have a complementary tab that is configured to securely fit into the slot of the spacing element 330. In another embodiment, the spacing element 330 can be attached to the inner surface section 310 with the use of clasps (e.g., button clasps).

Figure 2D:
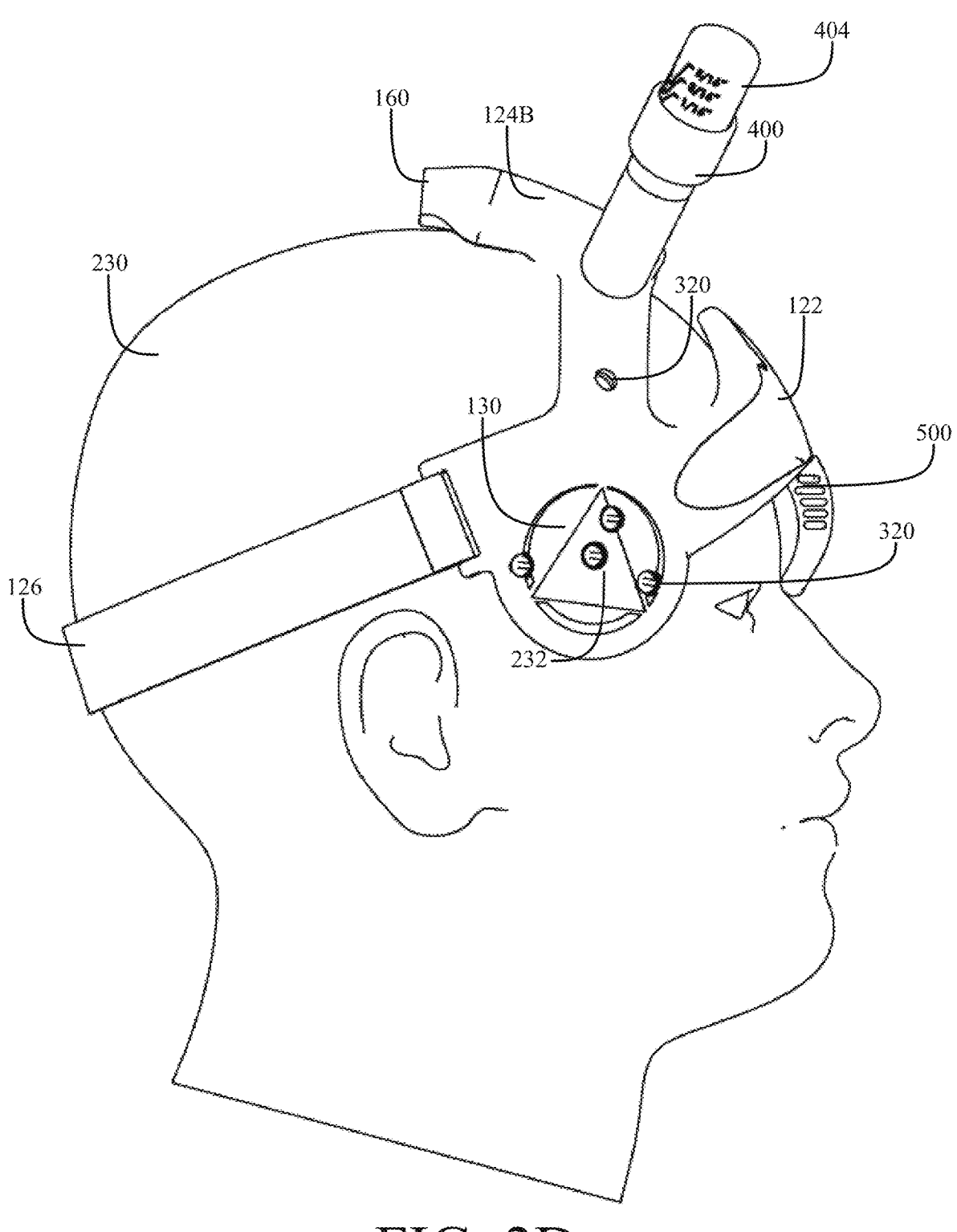
FIG. 2D depicts a profile view of another exemplary procedure for determining gap distances between the exemplary neuromodulation device and the head of the user including a fiducial landmark element, according to aspects of the present disclosure.
Figure 2E:
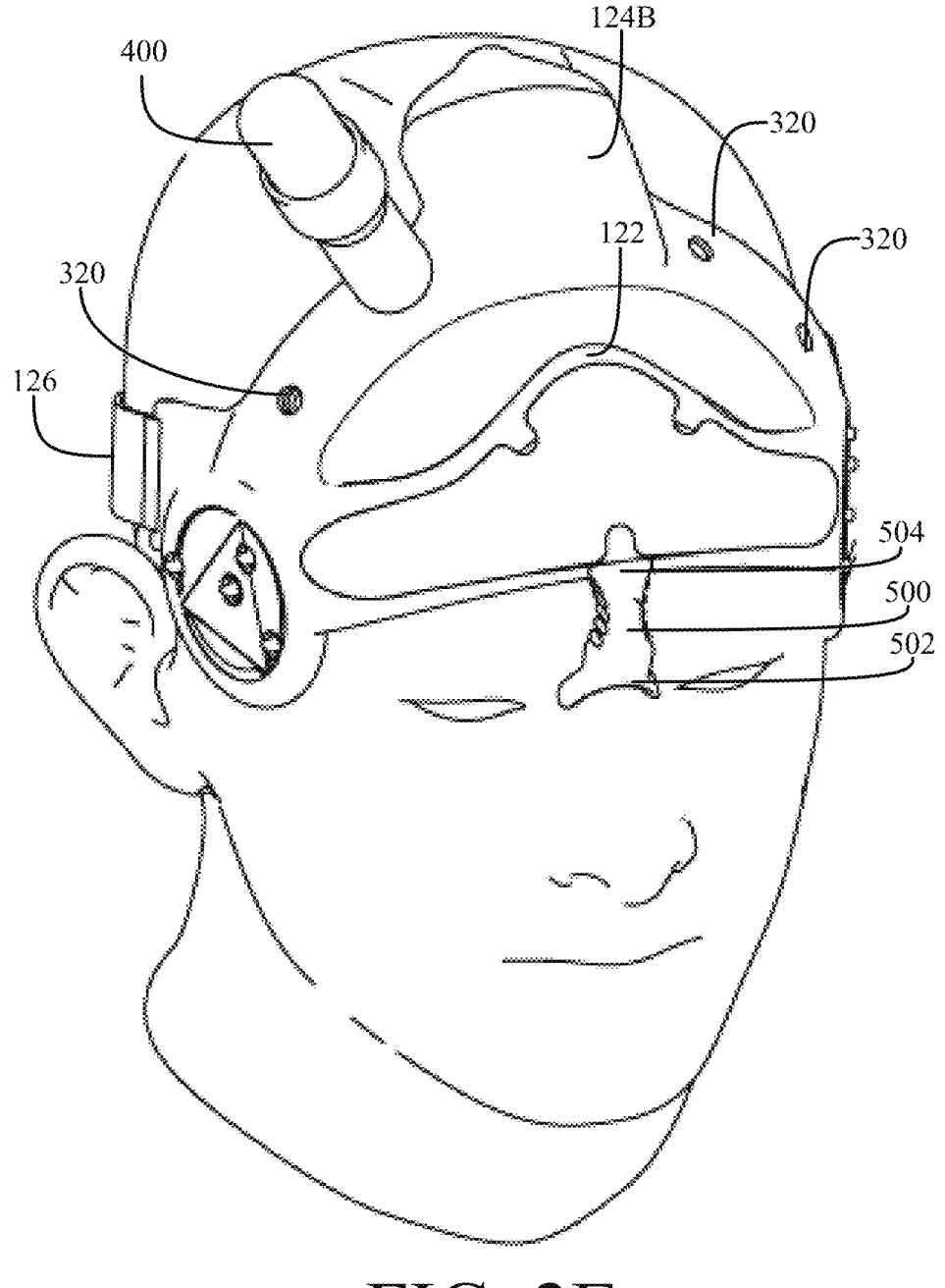
FIG. 2E depicts a front view of the exemplary procedure for determining gap distances between the exemplary neuromodulation device and the head of the user as shown in FIG. 2D, according to aspects of the present disclosure.

In some embodiments, as shown in FIGS. 2D-2E, the wearable device housing 120 can include a fiducial landmark element 500 that may be used to facilitate determining the initial position of the array housing 130 with respect to the temporal window 232 of the head 230 of the user. As best seen in FIG. 2E, in one embodiment of the fiducial landmark element 500, the fiducial landmark element can include a first end 504 that is coupled to the main band 122 and a second end 502 that is opposite the first end 504. The second end 502 can comprise a notch that is configured to receive a nose bridge of the user and the fiducial landmark element 500 can be positioned such that the second end 502 contacts the user at the end of the nose bridge. The position of the fiducial landmark element 500 can be determined during initial device imaging and registration, and according to at least some embodiments, the position of the ultrasound transducer elements 142 (within array housing 130) relative to the temporal window 232 of the user can be determined relative to the known position of the fiducial landmark element 500. It should be understood that fiducial landmark element 500 that is a nose bridge is one embodiment, and other fiducial landmark elements can be used such as those described in related U.S. Non-Provisional application Ser. No. 18/071,472, which is incorporated herein by reference. It should also be understood that the fiducial landmark element 500 can be made with physical variations to fit on a vast array or different human patient facial morphologies. In some embodiments, fiducial landmark element can be custom made for each user of neuromodulation device 110 for an optimal fit. In some embodiments, fiducial landmark element 500 can be constructed of a moldable material to allow a technician to custom mold the fiducial landmark element 500 to match the facial morphology of the user of the neuromodulation device 110.

It should be noted that while the exemplary embodiments discussed with respect to FIGS. 2A-2E discuss measuring the gap distance directly via a measurement tool, in other exemplary embodiments, the gap distance can be assessed without direct measurement. For example, the gap distance can be assessed subjectively by a trained technician based on overall fitment of the neuromodulation device 110 and/or other subjective fitment qualities that may be assessed by the technician. In some examples, the gap distance can be assessed subjectively by the user of neuromodulation device 110 based on subjective factors such as comfort, visual appearance, and/or other subjective fitment qualities that may be assessed by the user. Subjective assessment may be in place of, or complementary to, directly measuring the gap distance as described in reference to FIGS. 2A-2E.

FIG. 3 depicts the shift of an exemplary neuromodulation device between an initial placement on a user and a subsequent replacement of the neuromodulation device on the user. FIG. 3 also depicts an interior view of the wearable device housing 120, including conductive internal portion 125 of the secondary band 124 operatively connected by flexible circuit 127. Notably, the temporal window 232 of a user is shown below array housing 130 of wearable device housing 120. After following the procedure described with respect to FIGS. 2A-2E, the wearable device housing 120 can be taken off and refitted with the array housing 130 (and therefore the ultrasound transducer elements 142) located approximately at the same position as the initial position for which the initial user registration is performed. According to some embodiments, using the techniques described herein, the wearable device housing 120 is configured to shift no more than $\Delta X$ in the x direction and $\Delta Y$ in the y direction from the initial position. According to some embodiments, the total displacement from the initial position after subsequently refitting the wearable device housing 120 is no more than approximately 3 mm. That is, the user can take off and subsequently put back on wearable device housing 120 and the position of the ultrasound transducer elements 142 is displaced no more than 3 mm with to the temporal window 232 from the initial position, thereby ensuring effective and accurate beam formation at a target brain region upon subsequent refitting of the wearable device housing 120 to the head 230 of the user.

Embodiments of the neuromodulation device 110 are designed for a minimal form factor to facilitate comfortable wear for a user and to aid in the prevention of inadvertent shifting of the neuromodulation device with respect to the temporal window of the user when the device inadvertently contacts aspects of an external environment, such as when the device 110 comes into repeated contact with a pillow during sleep wear.

Conventional head-worn neuromodulation devices use independent cables or wires bonded to the rear of a multi-element array of ultrasound transducers. Flexible circuits are typically avoided due to the delicate nature of the circuit. Strain or bending of circuitry along multiple axes prevents conventional neuromodulation devices from incorporating a flexible circuit design, but typically would not preclude the use of individual wires bonded to the transducers which can bend freely. In contrast, the embodiment of neuromodulation device 110 as shown in FIG. 3 includes conductive portions 125 designed to maintain a primary degree of freedom within a flexible circuit 127 by providing a joint 129 within flexible circuit 127. As shown, joint 129 includes a primary degree of axial freedom of rotation which enables a primary bending mode of the cable. According to some example embodiments, the cable may also have a more limited twisting mode. Twisting of the cable may be limited by design, because excess twisting of the cable may damage circuit traces over time. Due to the positionings of the band housing 123, the position of joint 129 within band 124 allow for fitment of various human head shapes while facilitating the use of a flexible circuit 127 in place of micro wires, which increase the complexity and failure rate of neuro-modulation devices. In other words, the neuromodulation device 110 can bend along the anterior to posterior axis defined by joint 129 to allow the device to fit both wide and narrow head sizes. By including flexible circuit 127 joined by joint 129 along the head surface in congruency with the bending axis of joint 129, the form factor is maintained and optimized. Specifically, as shown in FIG. 3, the conductive internal portion 125 exits the transducer housing 130 and runs parallel to the surface of the head of the user between a position approximate the temporal window, to a top-contact point on the head. The flex circuit 127 lies relatively flat in the band housing 123 which is designed to not bend along the medial to lateral axis direction, thereby protecting the integrity of flexible circuit 127.

Figure 4:
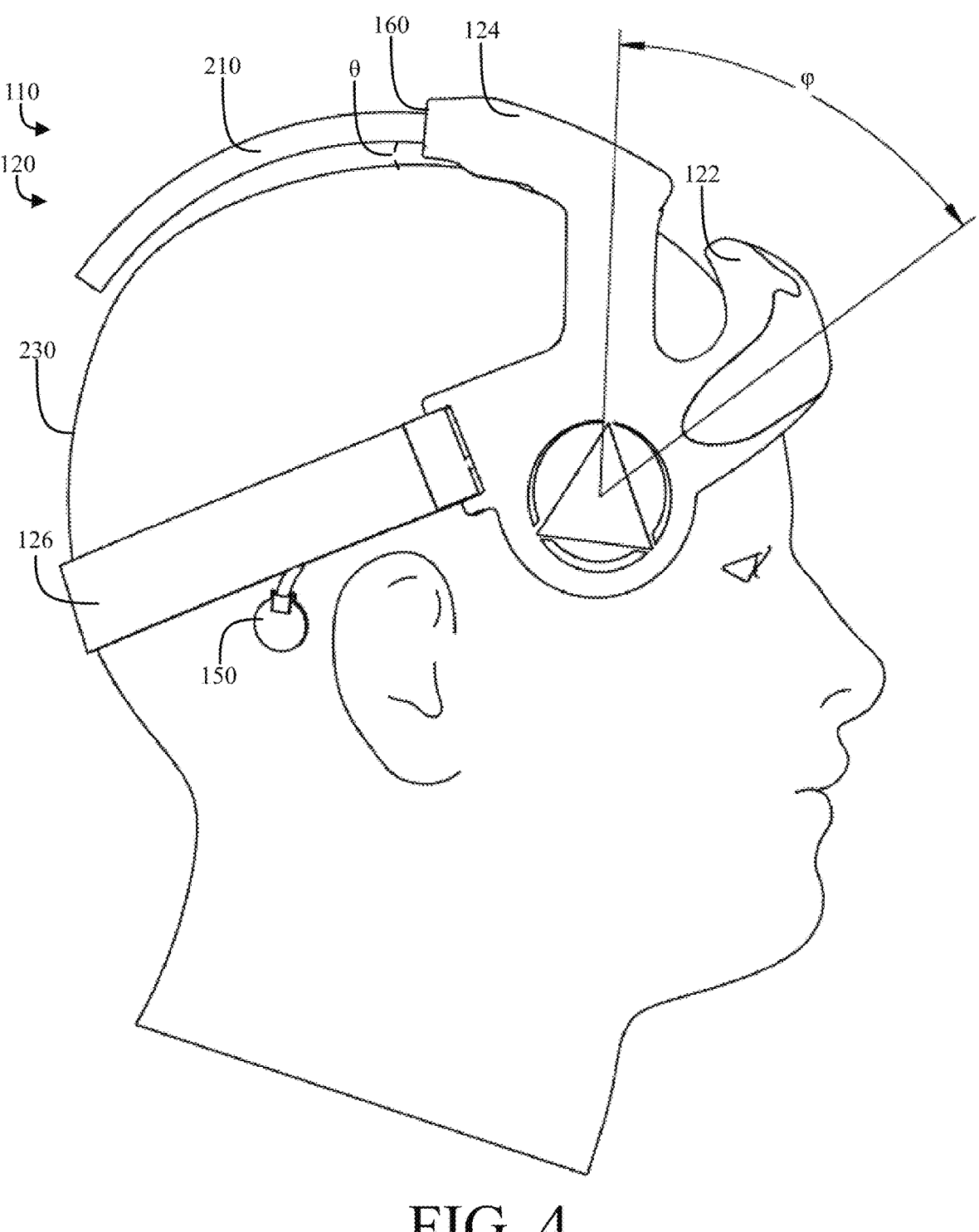
FIG. 4 depicts angular relationships between the first band and the second band of an exemplary neuromodulation device and the electrical cabling of the exemplary neuromodulation device and the head of the user, according to aspects of the present disclosure.

FIG. 4 depicts angular relationships between the first band and the second band of an exemplary neuromodulation device and the electrical cabling of the exemplary neuro-modulation device 110 and the head 230 of the user. As shown, a frontal contact point of the head of a user contacts the main band 122 and a top contact point of the head of a user contacts the secondary band 124. The arc between the frontal contact point and the top contact point can create an angle φ. According to some embodiments, the angle φ can be between approximately 45° and approximately 55°, as will be described in more detail with reference to FIGS. 6A-6B and 7A-7B, below. The angle φ has been experimen-tally shown to provide the best fit of the wearable device housing 120 to the head 230 of the user such perturbations of the wearable device housing 120 cause little to no movement of the ultrasound transducer elements 142 with respect to the temporal window 232 of the user, as is described in more detail below with respect to FIGS. 6A-6B and 7A-7B. In addition, conductive wiring 210 is shown exiting cable port 160 and forming an angle θ between the conductive wiring 210 and the parallel surface of the top of the head 230 of the user. According to some embodiments, angle θ may be approximately 15° or less. Angle θ provides numerous advantages. For example, keeping the conductive wiring close to but not teaching the head 230 of the user keeps the conductive wiring 210 out of the way of the user and minimizes discomfort surrounding extended wear of the neuromodulation device 110, for example when wearing the neuromodulation device 110 during sleep.

FIGS. 5A-5F depict experimental results of reliably returning the ultrasound transducer elements 142 of the wearable device housing 120 to the initial position with respect to the temporal window 232. More specifically, FIG. 5A shows an initial placement of the ultrasound transducer array 140 at f0. Subsequently, the neuromodulation device 110 was taken off the user and replaced on the user and the position of the ultrasound transducer array was recorded at position f1, f2, and f3. Each time the neuromodulation device 110 was refit to the user, the total displacement along the x, y axes was less than 3 mm. FIG. 5B shows the measured placement error in millimeters. The median and mean error were found to be less than 3 mm. FIG. 5C shows the relationship between the simulated x placement error in mm and the simulated y placement error in mm. FIG. 5C shows that there is no strong correlation between x place-ment error and y placement error. FIG. 5D shows the relationship between the positional error (in mm) versus the relative peak pressure produced by the ultrasound transducer elements 142 at a target brain area. As shown, at the maximum expected positional error (3 mm), the relative peak pressure is approximately 80% of the peak pressure produced when the ultrasound transducer elements 142 are aligned with the initial position relative to the temporal window, which is sufficient for good performance of the neuromodulation device 110. FIG. 5E shows the relationship between the positional error (in mm) versus the beam volume, where a smaller, more concentrated beam volume is desirable. As shown, at the maximum expected positional error (3 mm), the beam volume is approximately 0.6 cm³, which is only approximately a 20% difference in beam volume, sufficient for good performance of the neuromodu-lation device 110. FIG. 5F shows a cross section of the beam formed by ultrasound transducer elements 142 with a 0 mm displacement from the initial position relative to the tem-poral window and a 3 mm displacement from the initial position relative to the temporal window. As shown, even with a 3 mm positional error, the target brain area (in this embodiment, the subthalamic nucleus) is still within the beam volume produced by the neuromodulation device 110.

Figure 6A:
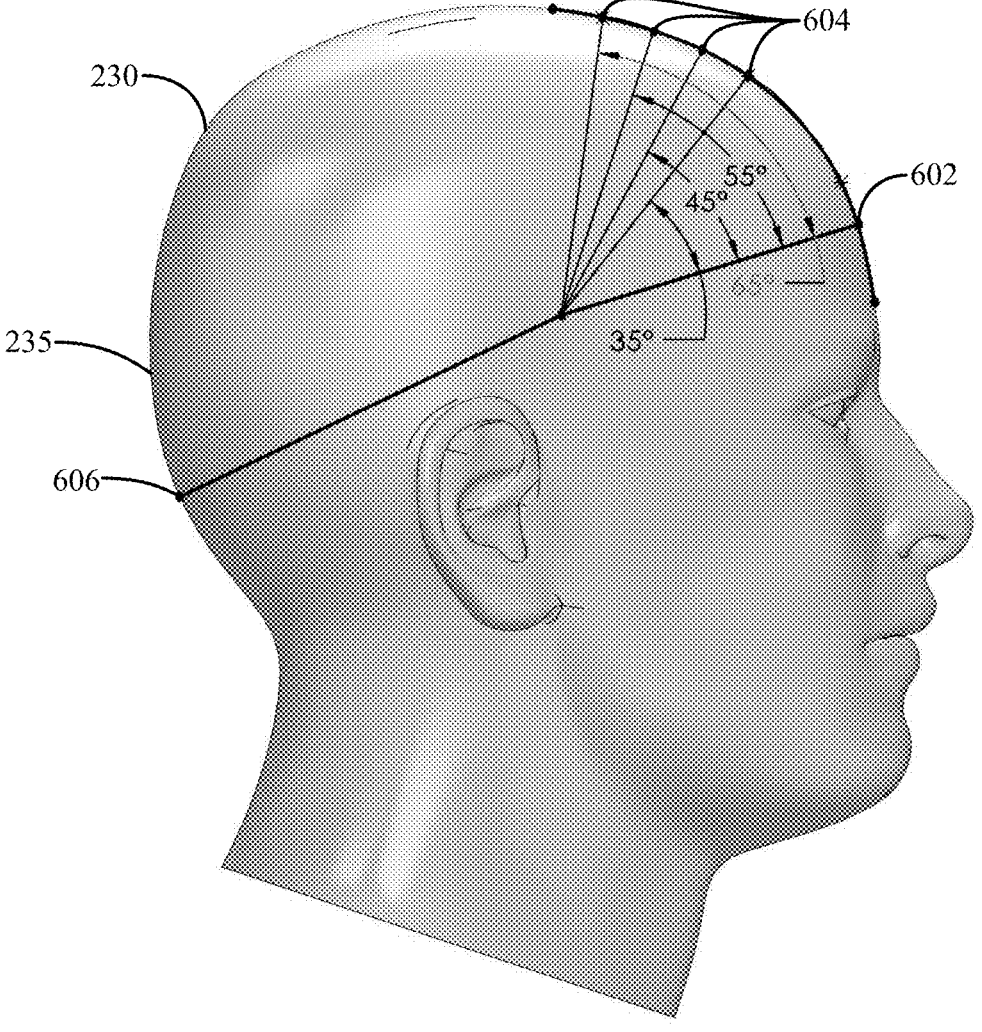
FIG. 6A illustrates the angular relationship between a frontal contact point and a top contact point of an exemplary neuromodulation device and contact points of the head of an exemplary user of the neuromodulation device, according to aspects of the present disclosure.

According to some embodiments consistent with this disclosure, specific design elements were identified for bal-ancing the moments generated by portions of the neuro-modulation device 110, such as the main band 122, second-ary band 124, and securing strap 126, as will be explained in further detail with reference to FIGS. 6A-6B. Referring now to FIG. 6A, a point in physical space at the front of the forehead of a user at which the main band 122 makes contact with head 230 of the user is a frontal contact point 602. A medial location on top of the head 230 of a user at which the secondary band 124 makes contact with head 230 of the user is a top contact point 604. A posterior location on top of the head 230 of a user at which the strap 126 makes contact with head 230 of the user is a rear contact point 606. The rear contact point 606 is located on the back of the head below the inion 235. The inion 235 is a physical landmark under-stood as the bony protrusion found on the midline of the occipital bone at the lower rear part of the skull. As used herein, a contact point refers to the center of mass or most medial points of physical contact of any component of the device 110 with the head 230 of the user. Device compo-nents refer to any solid or fluid material comprising the device, including but not limited to device housing, transducers, foam or silicone padding, and gels or coupling agents included as part of neuromodulation device 110.

Figure 6B:
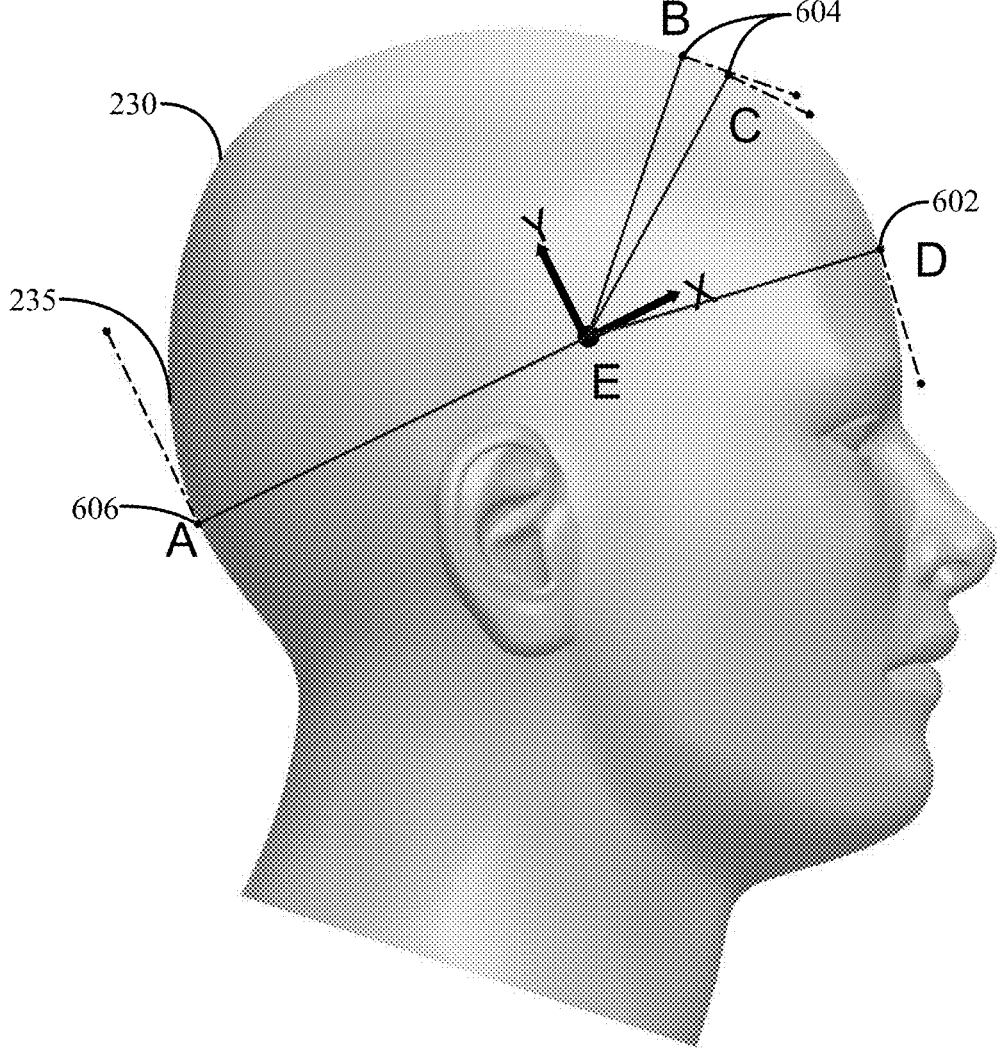
FIG. 6B illustrates an acceptable range of angles for the angle formed between a top contact point and a front contact point of an exemplary neuromodulation device, according to aspects of the present disclosure.

Referring now to FIG. 6B, let E serve as the center of forces for neuromodulation device 110 when being worn on head 230 of a user. Y and X define a local coordinate system such that E is understood as the center of forces, e.g., the origin of a local coordinate system from which a central force originates. The center of forces E between contact points 602, 604, and 606, forms on both sides of the head 230 superior to or approximate to the ultrasound transducers located at the temporal window of the user. These two points, E, one on either side of the head, serve as the intersection line of equilibrium between the frontal contact point 602 and the top contact point 604. Also shown are force contribution A, resulting from the contact between neuromodulation device 110 at rear contact point 606, force contributions D, resulting from the contact between neuromodulation device 110 at frontal contact point 602, and force contributions B and C resulting from the contact between neuromodulation device 110 at top contact point 604. Note that force contributions B and C show the outer bound of stable positions of contact for the neuromodulation device 110 at top contact point 604, with force contribution B associated with an approximately 55° angle between main band 122 and secondary band 124 and force contribution C associated with an approximately 45 angle between main band 122 and secondary band 124. Force contributions B/C and D tend to cause the neuromodulation device 110 to rotate clockwise, while force contribution A tends to cause the neuromodulation device 110 to rotate counterclockwise around head 230 of a user. As shown, Force contributions B, C, and D may form an approximate right angle with respect to the normal of the head surface. Through iterative investigation of device stability of neuromodulation device 110, the design shown in FIGS. 7A-7B was identified which maintains a narrow angle range between the three center of forces A, B/C, and D, and the contact points 602, 604, and 606.

It should be noted that the position of the rear contact point 606 and the frontal contact point 602 were approximated based on the highly conserved head geometry of the inion and forehead, as well as the requirements of the ultrasound sensors of the neuromodulation device 110. By way of analogy, the design can be considered analogous to a string system for purposes of flexible material force distribution. For the force vectors A, B/C, and D resulting from contact between the device and the head 230 of the user at contact points 602, 604, and 606 to be balanced, these force vectors ideally maintain an orientation that is perpendicular to the normal from the surface of the head 230 (e.g., parallel with the surface at the head at the respective contact point).

The stability of the ultrasound transducer elements 142 about the center of forces E was assessed while varying the angle φ between the frontal contact point 602 and top contact point 604. It was found that deviations in the normality of force vectors A, B/C, and D caused the neuromodulation device 110 to migrate or slip towards a position in which normality was net maximized across contact points 602, 604, and 606. It was also found that the contact points 602, 604, and 606 become less perpendicular relative to the surface of the skull and result in increasing force contributions, inherently destabilizing the ultrasound transducer elements 142 location relative to a user's temporal window. Through experimentation, an acceptable minimum and maximum angle φ was determined to be between approximately 45 and 55 degrees to minimize device migration or slippage. It was determined that an obtuse angle was needed between rear contact point 606 and the top contact point 604 for the neuromodulation device 110 to be in force balance. Even minute device migration or slippage can result in the inaccurate placement of the neuromodulation device 110 relative to a correct position for creating an ultrasound focus at a target brain area.

A second key discovery was that deviation of the angle φ below approximately 45 or above approximately 55 increases required force contribution of the top contact point vector to balance the device. This was true for all head geometries studied, indicating that the optimal range for angle φ is conserved among the majority of the human population. Due to the angle between contact point 606 and contact point 604 is obtuse, the force vector A and B/C resist the force contact vector D from pulling or pushing the wearable in the posterior or anterior direction.

Figures 7A, 7B:
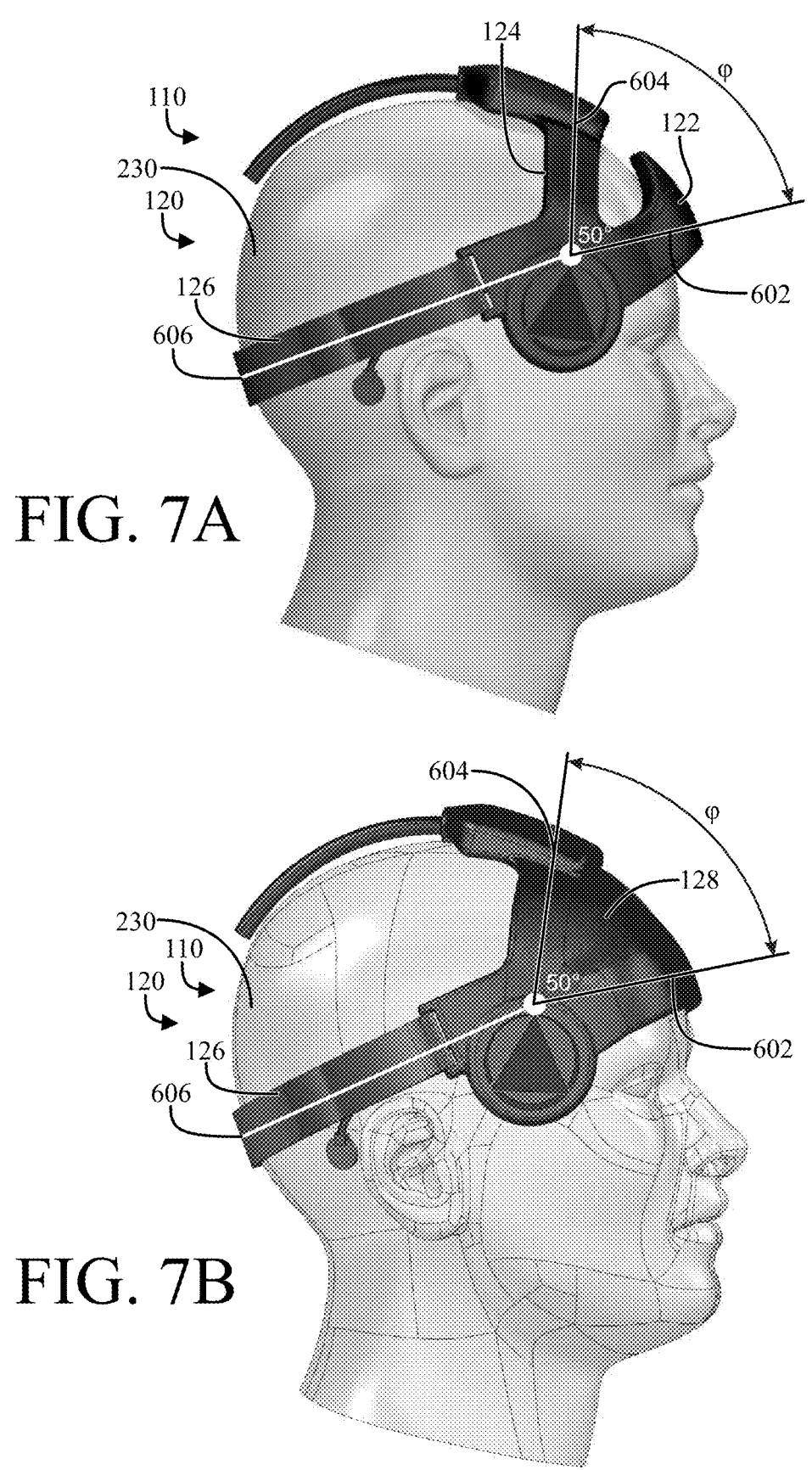
FIG. 7A depicts an exemplary neuromodulation device having a first band contacting the head of a user at a frontal contact point, a second band contacting the head of a user at a top contact point, and a strap contacting the head of a user at a rear contact point, according to aspects of the present disclosure.
FIG. 7B depicts an exemplary neuromodulation device having a single band contacting the head of a user at a frontal contact point and at a top contact point and a strap contacting the head of a user at a rear contact point, according to aspects of the present disclosure.

FIGS. 7A-7B show two exemplary embodiments of neuromodulation device 110. As shown in FIG. 7A, wearable housing 120 includes a main band 122 contacting the head of a user at a frontal contact point 602 and a secondary band 124 contacting the head of a user at a top contact point 604, and securing strap 126 contacting the head of a user at a rear contact point 606. In contrast to FIG. 7A, FIG. 7B shows a neuromodulation device 110 with a variation in the wearable housing 120. The wearable housing 120 includes a single band 128 that contacts the head of a user at a frontal contact point 602 and to contact point 604. Note that in both embodiments shown in FIGS. 7A-7B, the angle φ being maintained between approximately 45 and 55 degrees ensures that the moment of inertia is minimized, thereby minimizing the likelihood of neuromodulation device 110 shifting such that an ultrasound focus generated by the neuromodulation device 110 is attenuated during wear/use. It should also be understood that in some embodiments (not shown), wearable housing 120 can comprise a unitary cap that extends from approximately frontal contact point 602 of a user's head towards rear contact point 606 of the user's head.

The disclosed embodiments may be implemented according to at least the following clauses:

Clause 1: A method may include: providing a head-mounted device may include: an ultrasound transducer element housing; and one or more ultrasound transducer elements positioned within the ultrasound transducer element housing; fitting the head-mounted device to a head of a user such that the one or more ultrasound transducer elements are positioned in a first position approximate a temple of the user; focusing ultrasonic energy emitted by the one or more ultrasound transducer elements to a target brain region within the head of the user such that at least one ultrasound focus is created approximate the target brain region; and reliably refocusing ultrasonic energy emitted by the one or more ultrasound transducer elements to the target brain region such that at least one ultrasound focus is recreated approximate the target brain region after the head-mounted device is removed from and subsequently refitted to the head of the user.

Clause 2: The method as clause 1 describes, where the head-mounted device further may include a plurality of medial contact points may include at least one contact point approximate a forehead of the user and at least one contact point approximate a top of the head of a user, where the at least one contact point approximate the forehead of the user and the at least one contact point approximate the top of the head of the user forms an angle between approximately 45 degrees and approximately 55 degrees.

Clause 3: The method as either of clauses 1 or 2 describe, where: the head-mounted device further may include a band coupled to the ultrasound transducer element housing and extending behind a rear of the head of the user; the plurality of medial contact points further may include a rear contact point at which the head-mounted device contacts the head of the user; and the rear contact point is positioned below an inion of the head of the user.

Clause 4: The method as any of clauses 1-3 describe, where the head-mounted device further may include one or more fiducial landmark elements, the method further may include: imaging the head of the user and the head-mounted device to determine a position of the one or more fiducial landmark elements with respect to the head of the user; and mapping a position of the one or more ultrasound transducer elements relative to the temple of the user based on the position of the one or more fiducial landmark elements.

Clause 5: The method as any of clauses 1-4 describe, where the head-mounted device further may include a fiducial contact piece for aligning the head-mounted device, the fiducial contact piece may include a first end and a second end opposite the first end, the first end coupled to the head-mounted device and the second end configured to extend approximate to a cranial landmark of the user.

Clause 6: The method as any of clauses 1-5 describe, where the cranial landmark is selected from one or more eyes, a chin, a nose, one or more ears, a jaw, a mouth, one or more teeth, a tragus, and one or more eyebrows.

Clause 7: The method as any of clauses 1-6 describe, where the head-mounted device further may include a fiducial contact piece for aligning the head-mounted device, the fiducial contact piece may include a first end and a second end opposite the first end, the first end coupled to the head-mounted device and the second end having a notch for receiving a nose bridge of the user, where fitting the head-mounted device to the head of the user further may include positioning the second end of the fiducial contact piece to contact the user approximate to the nose bridge between eyes of the user.

Clause 8: The method as any of clauses 1-7 describe, further may include removing the head-mounted device from the head of the user and subsequently refitting the head-mounted device to the head of the user such that the one or more ultrasound transducer elements return to approximately the first position approximate the temple of the user.

Clause 9: The method as any of clauses 1-8 describe, where the one or more ultrasound transducer elements return to a second position that is less than approximately 4 mm from the first position.

Clause 10: The method as any of clauses 1-9 describe, further may include: simulating an acoustic wave propagation between the target brain region and the one or more ultrasound transducer elements, where focusing ultrasonic energy emitted by the one or more ultrasound transducer elements may include computing and applying a phase change to ultrasound emissions from the one or more ultrasound transducer elements such that at least one ultrasound focus is created at the target brain region based on the simulating, and where refocusing ultrasonic energy emitted by the one or more ultrasound transducer elements may include reliably applying the computed phase of ultrasound emissions from the one or more ultrasound transducer elements such that at least one ultrasound focus is recreated at the target brain region after the head-mounted device is removed from and subsequently refitted to the head of the user such that the one or more ultrasound transducer elements are positioned in approximately the first position.

Clause 11: The method as any of clauses 1-10 describe, where the head-mounted device further may include: a first band coupled to the ultrasound transducer element housing and extending over a top of the head of the user; and electrical cabling configured to control the one or more ultrasound transducer elements; where the electrical cabling is routed through the first band and exits the first band on a posterior facing side of the first band at an angle of no more than 15 degrees relative to a parallel surface of the top of the head of the user.

Clause 12: The method as any of clauses 1-11 describe, where in the head-mounted device further may include a first band coupled to the ultrasound transducer element housing and extending over a top of the head of the user, the first band may include: one or more inner surface sections configured to receive one or more spacing elements; an outer surface may include one or more apertures through the first band respectively positioned above a spacing element of the one or more spacing elements; and one or more spacers configured to attach to a respective inner surface section of the one or more inner surface sections.

Clause 13: The method as any of clauses 1-12 describe, further may include: assessing a gap distance between the head of the user and each of the one or more inner surface sections; selecting one or more spacing elements based on the assessed gap distances between the head of the user and each of the one or more inner surface sections; and attaching each of the one or more spacing elements to a respective inner surface section of the one or more inner surface sections.

Clause 14: The method as any of clauses 1-13 describe, further may include measuring the gap distances through the one or more apertures with a measurement tool.

Clause 15: The method as any of clauses 1-14 describe, where the measurement tool is selected from a depth gauge and an optical distance sensor.

Clause 16: A head-mounted device may include: an ultrasound transducer element housing; one or more ultrasound transducer elements positioned within the ultrasound transducer element housing and configured to be positioned in a first position approximate a temple of a user when the head-mounted device is worn on a head of the user; and at least one processor programmed with instructions that when executed by the at least one processor cause the at least one processor to control the one or more ultrasound transducer elements to focus ultrasonic energy emitted by the one or more ultrasound transducer elements to create at least one ultrasound focus approximate to at least one target region within the head of the user wearing the head-mounted device and reliably refocus ultrasonic energy emitted by the one or more ultrasound transducer elements to the at least one target region such that the at least one ultrasound focus is recreated approximate to the at least one target region after the head-mounted device is removed from and subsequently refitted to the head of the user.

Clause 17: The head-mounted device as clause 16 describes, where the head-mounted device further may include a plurality of medial contact points may include at least one contact point approximate a forehead of the user and at least one contact point approximate a top of the head of the user, and where the at least one contact point approximate to the forehead of the user and the at least one contact point approximate the top of the head of the user forms an angle between approximately 45 degrees and approximately 55 degrees.

Clause 18: The head-mounted device as either of clauses 16 or 17 describe where: the head-mounted device further may include a band coupled to the ultrasound transducer element housing and extending behind a rear of the head of the user; the plurality of medial contact points further may include a rear contact point at which the head-mounted device contacts the head of the user; and the rear contact point is positioned below an inion of the head of the user.

Clause 19: The head-mounted device as any of clauses 16-18 describe, further may include a fiducial contact piece for aligning the head-mounted device, the fiducial contact piece may include a first end and a second end opposite the first end, the first end coupled to the head-mounted device and the second end having a notch for receiving a nose bridge of the user, and where fitting the head-mounted device to the head of the user may include positioning the second end of the fiducial contact piece to contact the user at the end of the nose bridge between eyes of the user.

Clause 20: The head-mounted device as any of clauses 16-19 describe, where a position of the one or more ultrasound transducer elements are mapped relative to the temple of the user by imaging the head of the user and the head-mounted device worn by the user.

Clause 21: The head-mounted device as any of clauses 16-20 describe, further may include: a band coupled to the ultrasound transducer element housing and extending over a top of a head of the user; and electrical cabling configured to control the one or more ultrasound transducer elements, where the electrical cabling is routed through the first band and exits the first band on a posterior facing side of the first band at an angle of no more than 15 degrees relative to a parallel surface of the top of the head of the user.

Clause 22: A head-mounted device mays include: an ultrasound transducer element housing; one or more ultrasound transducer elements positioned within the ultrasound transducer element housing; and at least one band configured to secure the device to a head of a user, the at least one band may include: one or more conductive internal band portion operatively connected to the ultrasound transducer elements; a band housing disposed approximate to a top of the head of the user; a flexible circuit disposed within the band housing and operatively connecting the one or more conductive internal band portions; and a flexible joint of the flexible circuit, where the flexible joint enables a primary bending mode of the flexible circuit.

Clause 23: The head-mounted device as clause 22 describes, where the primary bending mode of the flexible circuit enables the at least one band to flex to accommodate varying head sizes of users without compromising integrity of the flexible circuit.

Clause 24: The head mounted device as either of clause 22 or 23 describe, where the flexible joint defines an anterior to posterior axis about which the flexible circuit is configured to flex.

The foregoing is merely illustrative of the principles of this disclosure and various modifications may be made by those skilled in the art without departing from the scope of this disclosure. The above-described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

As a further example, variations of apparatus or process parameters (e.g., dimensions, configurations, components, process step order, etc.) may be made to further optimize the provided structures, devices, and methods, as shown and described herein. In any event, the structures and devices, as well as the associated methods, described herein have many applications. Therefore, the disclosed subject matter should not be limited to any single embodiment described herein, but rather should be construed in breadth and scope in accordance with the appended claims.

The terms "about" and "approximately" shall generally mean an acceptable degree of error or variation for the quantity measured given the nature or precision of the measurements. Typical, exemplary degrees of error or variation are within 20 percent (%), preferably within 10%, more preferably within 5%, and still more preferably within 1% of a given value or range of values. Numerical quantities given in this description are approximate unless stated otherwise, meaning that the term "about" or "approximately" can be inferred when not expressly stated.

With reference to the use of the word(s) "comprise," "comprises," and "comprising" in the foregoing description and/or in the following claims, unless the context requires otherwise, those words are used on the basis and clear understanding that they are to be interpreted inclusively, rather than exclusively, and that each of those words is to be so interpreted in construing the foregoing description and/or the following claims.

The term "including" should be interpreted to mean "including but not limited to . . ." unless the context clearly indicate otherwise.

The term "consisting essentially of" means that, in addition to the recited elements, what is claimed may also contain other elements (steps, structures, ingredients, components, etc.) that do not adversely affect the operability of what is claimed for its intended purpose. Such addition of other elements that do not adversely affect the operability of what is claimed for its intended purpose would not constitute a material change in the basic and novel characteristics of what is claimed.

The term "adapted to" means designed or configured to accomplish the specified objective, not simply able to be made to accomplish the specified objective.

The term "capable of" means able to be made to accomplish the specified objective.

The terminology used herein is for the purpose of describing particular embodiments only and is not intended to be limiting. As used herein, the singular forms "a", "an" and "the" are intended to include the plural forms as well (i.e. "at least one"), unless the context clearly indicates otherwise.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

Terms such as "at least one of A and B" should be understood to mean "only A, only B, or both A and B." The same construction should be applied to longer list (e.g., "at least one of A, B, and C").

The term contact point refers to the center of mass or most medial point of contact of any device component it interfaces with the head, hair, or scalp.

The term device component encompasses the device itself, as well as any material or coupling agents used with the device. The term head refers to hair, scalp, and/or third party products that contact the hair and/or scalp.

The term medial refers to the center point in both the anterior/posterior and medial/lateral planes, wherein medial refers to features towards the midline of the body. For example, the nose is medial to the ears.

The term lateral refers to an outside point in the medial/lateral planes. For example, the ears are lateral to the nose.

The term anterior to posterior refers to the axis from the back to the front of the head or face. For example, the eyes are located on an anterior side of the head, whereas the inion is located at the posterior side of the head.

The term "focus" refers to any position within an ultrasonic pressure field which reaches a pressure of at least 30% of the peak possible pressure for the given ultrasonic pressure field at a target brain region. The term "refocus" refers to recreating a focus approximate the target brain region.

The term "fiducial" refers to an object or item serving as a landmark that is used to identify a physical location of one objects and/or one or more mechanically independent objects. More specifically, the term fiducial can refer to an object or item serving as a landmark that is used to determine the physical location of an object relative to the landmark.

The term "nose bridge" refers to the upper, bony part of the nose, which overlies the nasal bones. In human subjects, the nose bridge is located approximately between the eyes.

The "approximate" refers to when one object is adjacent to, nearby, or touching another object.

What is claimed is:

1. A method comprising:
   providing a head-mounted device comprising:
       an ultrasound transducer element housing; and
       one or more ultrasound transducer elements positioned within the ultrasound transducer element housing;
   fitting the head-mounted device to a head of a user such that the one or more ultrasound transducer elements are positioned in a first position approximate a temple of the user;
   focusing ultrasonic energy emitted by the one or more ultrasound transducer elements to a target brain region within the head of the user such that at least one ultrasound focus is created approximate the target brain region; and
   reliably refocusing ultrasonic energy emitted by the one or more ultrasound transducer elements to the target brain region such that at least one ultrasound focus is recreated approximate the target brain region after the head-mounted device is removed from and subsequently refitted to the head of the user.

2. The method of claim 1, wherein the head-mounted device further comprises a plurality of medial contact points comprising at least one contact point approximate a forehead of the user and at least one contact point approximate a top of the head of a user, wherein the at least one contact point approximate the forehead of the user and the at least one contact point approximate the top of the head of the user forms an angle between approximately 45° and approximately 55°.

3. The method of claim 2, wherein:
   the head-mounted device further comprises a band coupled to the ultrasound transducer element housing and extending behind a rear of the head of the user;
   the plurality of medial contact points further comprise a rear contact point at which the head-mounted device contacts the head of the user; and the rear contact point is positioned below an inion of the head of the user.

4. The method of claim 1, wherein the head-mounted device further comprises one or more fiducial landmark elements, the method further comprising:
   imaging the head of the user and the head-mounted device to determine a position of the one or more fiducial landmark elements with respect to the head of the user; and
   mapping a position of the one or more ultrasound transducer elements relative to the temple of the user based on the position of the one or more fiducial landmark elements.

5. The method of claim 1, wherein the head-mounted device further comprises a fiducial contact piece for aligning the head-mounted device, the fiducial contact piece comprising a first end and a second end opposite the first end, the first end coupled to the head-mounted device and the second end configured to extend approximate to a cranial landmark of the user.

6. The method of claim 5, wherein the cranial landmark is selected from one or more eyes, a chin, a nose, one or more ears, a jaw, a mouth, one or more teeth, a tragus, and one or more eyebrows.

7. The method of claim 1, wherein the head-mounted device further comprises a fiducial contact piece for aligning the head-mounted device, the fiducial contact piece comprising a first end and a second end opposite the first end, the first end coupled to the head-mounted device and the second end having a notch for receiving a nose bridge of the user, wherein fitting the head-mounted device to the head of the user further comprises positioning the second end of the fiducial contact piece to contact the user approximate to the nose bridge between eyes of the user.

8. The method of claim 1, further comprising removing the head-mounted device from the head of the user and subsequently refitting the head-mounted device to the head of the user such that the one or more ultrasound transducer elements return to approximately the first position approximate the temple of the user.

9. The method of claim 8, wherein the one or more ultrasound transducer elements return to a second position that is less than approximately 4 mm from the first position.

10. The method of claim 1, further comprising:
   simulating an acoustic wave propagation between the target brain region and the one or more ultrasound transducer elements,
   wherein focusing ultrasonic energy emitted by the one or more ultrasound transducer elements comprises computing and applying a phase change to ultrasound emissions from the one or more ultrasound transducer elements such that at least one ultrasound focus is created at the target brain region based on the simulating, and
   wherein refocusing ultrasonic energy emitted by the one or more ultrasound transducer elements comprises reliably applying the computed phase of ultrasound emissions from the one or more ultrasound transducer elements such that at least one ultrasound focus is recreated at the target brain region after the head-mounted device is removed from and subsequently refitted to the head of the user such that the one or more ultrasound transducer elements are positioned in approximately the first position.

11. The method of claim 1, wherein the head-mounted device further comprises:

a first band coupled to the ultrasound transducer element housing and extending over a top of the head of the user; and electrical cabling configured to control the one or more ultrasound transducer elements;

wherein the electrical cabling is routed through the first band and exits the first band on a posterior facing side of the first band at an angle of no more than 15 degrees relative to a parallel surface of the top of the head of the user.

12. The method of claim 1, where in the head-mounted device further comprises a first band coupled to the ultrasound transducer element housing and extending over a top of the head of the user, the first band comprising:

one or more inner surface sections configured to receive one or more spacing elements;

an outer surface comprising one or more apertures through the first band respectively positioned above a spacing element of the one or more spacing elements; and one or more spacers configured to attach to a respective inner surface section of the one or more inner surface sections.

13. The method of claim 12, further comprising:

assessing a gap distance between the head of the user and each of the one or more inner surface sections;

selecting one or more spacing elements based on the assessed gap distances between the head of the user and each of the one or more inner surface sections; and attaching each of the one or more spacing elements to a respective inner surface section of the one or more inner surface sections.

14. The method of claim 13, further comprising measuring the gap distances through the one or more apertures with a measurement tool.

15. The method of claim 14, wherein the measurement tool is selected from a depth gauge and an optical distance sensor.

16. A head-mounted device comprising:

an ultrasound transducer element housing;

one or more ultrasound transducer elements positioned within the ultrasound transducer element housing and configured to be positioned in a first position approximate a temple of a user when the head-mounted device is worn on a head of the user; and at least one processor programmed with instructions that when executed by the at least one processor cause the at least one processor to control the one or more ultrasound transducer elements to focus ultrasonic energy emitted by the one or more ultrasound transducer elements to create at least one ultrasound focus approximate to at least one target region within the head of the user wearing the head-mounted device and reliably refocus ultrasonic energy emitted by the one or more ultrasound transducer elements to the at least one target region such that the at least one ultrasound focus is recreated approximate to the at least one target region after the head-mounted device is removed from and subsequently refitted to the head of the user.

17. The head-mounted device of claim 16, wherein the head-mounted device further comprises a plurality of medial contact points comprising at least one contact point approximate a forehead of the user and at least one contact point approximate a top of the head of the user, and wherein the at least one contact point approximate to the forehead of the user and the at least one contact point approximate the top of the head of the user forms an angle between approximately 45° and approximately 55°.

18. The head-mounted device of claim 17 wherein:

the head-mounted device further comprises a band coupled to the ultrasound transducer element housing and extending behind a rear of the head of the user;

the plurality of medial contact points further comprise a rear contact point at which the head-mounted device contacts the head of the user; and the rear contact point is positioned below an inion of the head of the user.

19. The head-mounted device of claim 16, further comprising a fiducial contact piece for aligning the head-mounted device, the fiducial contact piece comprising a first end and a second end opposite the first end, the first end coupled to the head-mounted device and the second end having a notch for receiving a nose bridge of the user, and wherein fitting the head-mounted device to the head of the user comprises positioning the second end of the fiducial contact piece to contact the user at the end of the nose bridge between eyes of the user.

20. The head-mounted device of claim 16, wherein a position of the one or more ultrasound transducer elements are mapped relative to the temple of the user by imaging the head of the user and the head-mounted device worn by the user.

21. The head-mounted device of claim 16, further comprising:

a band coupled to the ultrasound transducer element housing and extending over a top of a head of the user; and electrical cabling configured to control the one or more ultrasound transducer elements, wherein the electrical cabling is routed through the first band and exits the first band on a posterior facing side of the first band at an angle of no more than 15 degrees relative to a parallel surface of the top of the head of the user.

22. A head-mounted device comprising:

an ultrasound transducer element housing;

one or more ultrasound transducer elements positioned within the ultrasound transducer element housing; and at least one band configured to secure the device to a head of a user, the at least one band comprising:

one or more conductive internal band portion operatively connected to the ultrasound transducer elements;

a band housing disposed approximate to a top of the head of the user;

a flexible circuit disposed within the band housing and operatively connecting the one or more conductive internal band portions; and a flexible joint of the flexible circuit, wherein the flexible joint enables a primary bending mode of the flexible circuit.

23. The head-mounted device of claim 22, wherein the primary bending mode of the flexible circuit enables the at least one band to flex to accommodate varying head sizes of users without compromising integrity of the flexible circuit.

24. The head-mounted device of claim 22, wherein the flexible joint defines an anterior to posterior axis about which the flexible circuit is configured to flex.

* * * * *